(12) United States Patent
Chang

(10) Patent No.: US 9,895,255 B2
(45) Date of Patent: Feb. 20, 2018

(54) MULTILAYER FILM INCLUDING FOAM LAYER AND GAS BARRIER LAYER

(71) Applicant: Hollister Incorporated, Libertyville, IL (US)

(72) Inventor: Moh-Ching Oliver Chang, Lake in the Hills, IL (US)

(73) Assignee: HOLLISTER INCORPORATED, Libertyville, IL (US)

(*) Notice: Subject to any disclaimer, the term of this patent is extended or adjusted under 35 U.S.C. 154(b) by 445 days.

(21) Appl. No.: 14/226,260

(22) Filed: Mar. 26, 2014

(65) Prior Publication Data

US 2014/0205828 A1 Jul. 24, 2014

Related U.S. Application Data

(63) Continuation-in-part of application No. 13/835,499, filed on Mar. 15, 2013.
(Continued)

(51) Int. Cl.
*A61F 5/44* (2006.01)
*B32B 5/18* (2006.01)
(Continued)

(52) U.S. Cl.
CPC .......... *A61F 5/4404* (2013.01); *A61F 5/445* (2013.01); *B32B 27/065* (2013.01); *B32B 27/08* (2013.01); *B32B 27/304* (2013.01); *B32B 27/306* (2013.01); *B32B 27/34* (2013.01); *B32B 2266/025* (2013.01);
(Continued)

(58) Field of Classification Search
CPC combination set(s) only.
See application file for complete search history.

(56) References Cited

U.S. PATENT DOCUMENTS 4,376,799 A * 3/1983 Tusim .................. A61F 5/44
428/213
5,407,713 A 4/1995 Wilfong et al.
(Continued)

FOREIGN PATENT DOCUMENTS

EP 0958916 A2 11/1999
JP 2000255008 A 9/2000
(Continued)

OTHER PUBLICATIONS

International Search Report and Written Opinion for PCT/US2014/011102 dated Jun. 3, 2014.
(Continued)

*Primary Examiner* — Tatyana Zalukaeva
*Assistant Examiner* — Guy K Townsend
(74) *Attorney, Agent, or Firm* — Levenfeld Pearlstein, LLC

(57) ABSTRACT

A multilayer film includes an outer foam layer and a gas barrier layer. The multilayer film may also include at least one tie layer and at least one inner layer, and can be configured to have various film layer constructions. For example, the multilayer film can be configured as a five-layer, six-layer, or seven-layer films. The multilayer film can provide unique texture, softness, quietness, gas barrier properties, light weight and low cost per volume. Further, one or more layers of the multilayer film can contain a vinyl-bond rich triblock copolymer to provide sound absorbing properties.

16 Claims, 8 Drawing Sheets

Related U.S. Application Data

(60) Provisional application No. 61/755,709, filed on Jan. 23, 2013.

(51) Int. Cl.
*B32B 27/08* (2006.01)
*B32B 27/06* (2006.01)
*A61F 5/445* (2006.01)
*B32B 27/30* (2006.01)
*B32B 27/34* (2006.01)

(52) U.S. Cl.
CPC ... *B32B 2266/0242* (2013.01); *B32B 2270/00* (2013.01); *B32B 2307/102* (2013.01); *B32B 2307/702* (2013.01); *B32B 2307/7242* (2013.01); *B32B 2439/80* (2013.01); *Y10T 428/249953* (2015.04); *Y10T 428/249981* (2015.04); *Y10T 428/249982* (2015.04); *Y10T 428/249991* (2015.04)

(56) References Cited

U.S. PATENT DOCUMENTS

| | | | |
|---|---|---|---|
| 5,496,295 | A | 3/1996 | Wilfong et al. |
| 5,643,375 | A | 7/1997 | Wilfong et al. |
| 5,722,965 | A * | 3/1998 | Kuczynski ............... A61F 5/443 604/338 |
| 5,730,919 | A | 3/1998 | Wilfong et al. |
| 5,983,604 | A | 11/1999 | Wilfong et al. |
| 6,013,363 | A | 1/2000 | Takahashi et al. |
| 6,451,912 | B1 | 9/2002 | Kelch |
| 6,455,161 | B1 * | 9/2002 | Regnier ................... B32B 27/08 428/412 |
| 6,558,809 | B1 | 5/2003 | Kelch et al. |
| 6,559,234 | B1 * | 5/2003 | Arai ....................... C08F 210/02 525/241 |
| 6,579,584 | B1 | 6/2003 | Compton |
| 6,946,182 | B1 | 9/2005 | Allgeuer et al. |
| 7,070,852 | B1 | 7/2006 | Reiners et al. |
| 7,270,860 | B2 | 9/2007 | Giori |
| 7,279,532 | B2 | 10/2007 | Sasagawa et al. |
| 7,807,241 | B2 * | 10/2010 | Sasagawa ............... B32B 5/022 428/35.2 |
| 7,993,739 | B2 | 8/2011 | Barger et al. |
| 2002/0188065 | A1 | 12/2002 | Kelch |
| 2004/0126524 | A1 | 7/2004 | Longo et al. |
| 2007/0005032 | A1 * | 1/2007 | Shan ....................... A61F 5/448 604/342 |
| 2007/0237916 | A1 * | 10/2007 | Rasmussen ............. A61F 5/441 428/35.2 |
| 2008/0020162 | A1 | 1/2008 | Fackler et al. |
| 2010/0030167 | A1 | 2/2010 | Carsten et al. |
| 2010/0121290 | A1 | 5/2010 | Torben et al. |
| 2010/0210745 | A1 * | 8/2010 | McDaniel ............... C09D 5/008 521/55 |
| 2010/0330356 | A1 | 12/2010 | Jokisch |
| 2011/0250626 | A1 * | 10/2011 | Williams ............... A01N 63/02 435/18 |
| 2011/0285048 | A1 | 11/2011 | Barger et al. |
| 2012/0010580 | A1 * | 1/2012 | Forbes ..................... A61F 5/441 604/339 |
| 2012/0232504 | A1 * | 9/2012 | Chang ..................... A61F 5/445 604/332 |
| 2013/0045347 | A1 | 2/2013 | Kawasumi et al. |
| 2013/0143014 | A1 | 6/2013 | Kwasumi et al. |
| 2013/0221564 | A1 | 8/2013 | Allegaert et al. |
| 2013/0310782 | A1 * | 11/2013 | Chang ..................... A61F 5/441 604/333 |
| 2014/0205828 | A1 * | 7/2014 | Chang .................... B32B 27/065 428/220 |
| 2014/0207094 | A1 * | 7/2014 | Chang ................. A61L 28/0026 604/333 |
| 2014/0221950 | A1 * | 8/2014 | Chang ................. A61L 28/0034 604/332 |
| 2014/0221951 | A1 * | 8/2014 | Chang ..................... A61F 5/445 604/332 |
| 2014/0371698 | A1 * | 12/2014 | Chang ..................... A61F 5/445 604/333 |

FOREIGN PATENT DOCUMENTS

| | | |
|---|---|---|
| JP | 2003025518 A | 1/2003 |
| JP | 2005255830 A | 9/2005 |
| WO | 0100408 A1 | 1/2001 |
| WO | 2007093186 A1 | 8/2007 |

OTHER PUBLICATIONS

International Search Report issued by ISA/EPO in connection with PCT/US2015/17503 dated May 6, 2015.

* cited by examiner

MULTILAYER FILM INCLUDING FOAM LAYER AND GAS BARRIER LAYER

CROSS-REFERENCE TO RELATED APPLICATION DATA

This application is a continuation-in-part of U.S. application Ser. No. 13/835,499, filed Mar. 15, 2013 entitled "MULTILAYER FILM INCLUDING FOAM LAYER AND OSTOMY PRODUCTS MADE THEREFROM", which claims the benefit of priority of Provisional U.S. Patent Application Ser. No. 61/755,709, filed Jan. 23, 2013, the contents of which are incorporated fully by reference herein.

BACKGROUND

The present disclosure relates to multilayer films for ostomy products, and more particularly to multilayer films including a foamed layer having sound absorbing properties.

Ostomy appliances for collecting body waste, such as ostomy pouches, are used by patients who have had surgery such as a colostomy, ileostomy, or urostomy. Typically, an ostomy pouch includes two opposing walls, which are sealed around peripheral edges to define a cavity to collect body waste. Nonwovens have been commonly used with odor barrier films to make ostomy pouches. One example is a "3-layer" ostomy pouch including two layers of odor barrier films forming the opposing walls, and a nonwoven layer attached to the body side wall of the ostomy pouch. The nonwoven functions as a comfort panel to give soft touch feel to users and to reduce the wet slippery feel when the user perspires. Another example is a "4-layer" ostomy pouch including two layers of odor barrier films forming the opposing walls and two nonwoven layers, one attached to each of the walls.

Although nonwovens provide added comfort for users, there are some challenges in making ostomy pouches with nonwovens. For example, thickness variances for nonwovens are relatively greater than polymer films, which present process challenges in making ostomy pouches. Further, the process of maintaining consistent tension between a nonwoven and a film, and providing sufficient and precise energy to heat seal the nonwoven and the film are typically more complicated than between two polymeric films. Furthermore, the relatively high cost of nonwovens increases the cost to manufacture ostomy pouches which may result in increased costs to the user.

Another disadvantage of using nonwoven for ostomy pouches is that water can permeate through the nonwoven layer when a user takes a shower or swims. Further, when the nonwoven layer and the film layer are not laminated together, for example, sealed around their respective perimeters, the nonwoven layer is not very effective in reducing film noise.

In addition to providing comfort and softness, it is also highly desirable that ostomy pouches do not make noise during use for obvious reasons. Ostomy pouches that include a quiet film to reduce the noise produced by the pouches, for example, the plastic crackling sound made by the pouch when a user moves around, have been developed. Examples of such a quiet film include the multilayer films disclosed in Giori, U.S. Pat. No. 7,270,860, which is assigned to the assignee of the present application and incorporated herein in its entirety by reference.

When body waste is released from a stoma, flatus gas is often released together with the waste. The flatus gas passing through the stoma can cause a vibratory transient in body tissue, which is uncontrollable by the patient. Such release of the flatus gas from the stoma can accompany indiscreet noise, which can cause embarrassment to the patient. Conventional quiet films, however, could be improved upon to better insulate the flatus noise to prevent embarrassment.

Because of the inherent severe medical, social, and personal concerns related to the need for use of an ostomy appliance, improvements in ostomy appliances are desired. Any appreciable improvement in such ostomy appliances to provide greater discretion, privacy and comfort is of great importance in the quality of life of the increasing number of ostomy patients. The present disclosure provides improved ostomy appliances including a foam material that can replace conventional nonwoven layers according to various embodiments, to provide comfort and enhanced sound insulating properties.

BRIEF SUMMARY

A multilayer film including a gas barrier layer and an outer foam layer is provided according to various embodiments of the present disclosure. The multilayer film can provide unique texture, softness, quietness, gas barrier properties, light weight for thickness, and low cost per volume. Further, one or more layers of the multilayer film can contain a vinyl-bond rich triblock copolymer to provide improved sound absorbing properties. Thus, the multilayer film can be used to make ostomy pouches. Further, the multilayer film can be useful in other applications, such as food packaging films, oxygen/carbon dioxide/nitrogen barrier films, medical packaging films and as an alternative to nonwoven material.

In one aspect, a multilayer film including an outer foam layer and a gas barrier layer is provided. The multilayer film may have a modulus of about 2 ksi to about 40 ksi. Further, the multilayer film may also include at least one tie layer and at least one inner layer.

In one embodiment, the multilayer film may be configured as a six-layer film having a seal layer/tie layer/barrier layer/tie layer/inner layer/outer foam layer construction, or a seal layer/inner layer/tie layer/barrier layer/tie layer/outer foam layer construction. The inner layer may or may not be a foam layer.

In another embodiment, the multilayer film may be configured as a seven-layer film having a seal layer/tie layer/barrier layer/tie layer/inner layer/inner layer/outer foam layer construction, or a seal layer/inner layer/tie layer/barrier layer/tie layer/inner layer/outer foam layer construction. At least one of the inner layers may be a foam layer.

In yet another embodiment, the multilayer film may be configured as a five-layer film having a seal layer/tie layer/barrier layer/tie layer/outer foam layer construction.

The outer foam layer of any of the multilayer film embodiments may be formed from ethylene vinyl acetate (EVA), ethylene methyl acrylate (EMA), ethylene alpha olefin copolymers (ethylene based plastomers), ethylene based elastomers (olefin block copolymers, OBC), ethylene-propylene (EP) copolymers (PP-elastomer) or blends thereof. In one embodiment, the gas barrier layer is formed from a polymer blend comprising an amorphous polyamide and a functionalized rubber blend or compound. In some embodiments, at least one of the outer foam layer, inner layers, tie layers, and barrier layer may include a vinyl-bond rich triblock copolymer.

The multilayer layer film according to any of the embodiments may be configured to have a thickness of about 100 µm to about 500 µm.

Other aspects, objectives and advantages will become more apparent from the following detailed description when taken in conjunction with the accompanying drawings.

BRIEF DESCRIPTION OF THE DRAWINGS

The benefits and advantages of the present embodiments will become more readily apparent to those of ordinary skill in the relevant art after reviewing the following detailed description and accompanying drawings, wherein.

DETAILED DESCRIPTION

Figure 1:
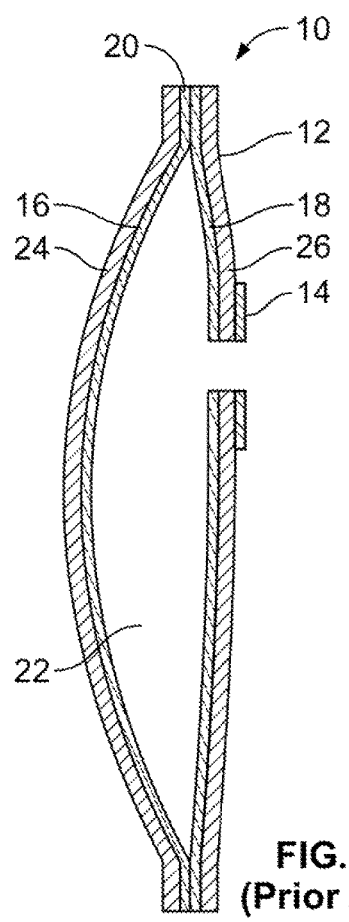
FIG. 1 is a cross-sectional illustration of a prior art ostomy appliance.

While the present disclosure is susceptible of embodiment in various forms, there is shown in the drawings and will hereinafter be described a presently preferred embodiment with the understanding that the present disclosure is to be considered an exemplification and is not intended to limit the disclosure to the specific embodiment illustrated.

FIG. 1 is a cross-sectional illustration of a prior art one-piece ostomy pouch 10. The ostomy pouch 10 generally includes a pouch 12 and a skin barrier 14. The pouch 12 includes first and second opposing walls 16, 18, which are sealed around peripheral edges 20 thereof to define a cavity 22 for collecting body waste. The pouch 12 also includes a first nonwoven layer 24 attached to the first wall 16, and a second nonwoven layer 26 attached to the second wall 18. The nonwoven layers 24, 26 are attached to the respective walls 16, 18 via heat sealing or an adhesive. Each of the first and second walls 16, 18 is formed of a suitable odor barrier film, which may be a single layer film or a multilayer film.

Typically, each side of the pouch is configured to have a total thickness of about 10 mil to about 16 mil. For example, each side includes a nonwoven layer heat sealed to a wall, in which the wall has a thickness of about 3 mil and the nonwoven layer has a thickness of about 11 mil to provide a total thickness of about 14 mil. In another example, each side includes a nonwoven layer attached to a wall by an adhesive therebetween, in which the wall has a thickness of about 2.25 mil, and the adhesive has a thickness of about 1.1 mil, and the nonwoven layer has a thickness of about 11 mil to provide a total thickness of about 14.35 mil.

Figure 2:
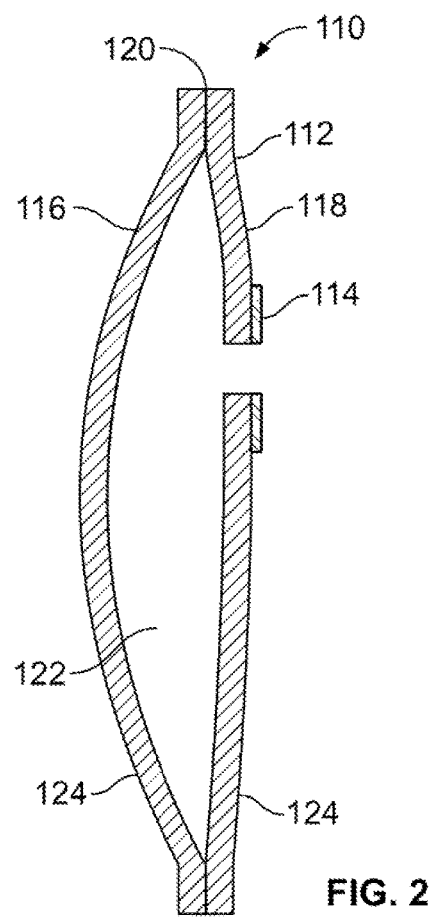
FIG. 2 is a cross-sectional illustration of an ostomy pouch according to an embodiment of the present disclosure.

FIG. 2 is a cross-sectional illustration of an embodiment of a one-piece ostomy pouch 110. The ostomy pouch 110 is similarly configured to the ostomy pouch 10 of FIG. 1, and generally includes a pouch 112 and a skin barrier 114. The pouch 112 includes first and second opposing walls 116, 118, which are sealed around peripheral edges 120 thereof by heat sealing or by any other suitable means to define a cavity 122 therebetween for collecting body waste.

Each of the first and second walls 116, 118 is formed of a multilayer composite film 124. The composite film 124 is designed to replace the film/nonwoven construction or the film/adhesive/nonwoven construction of prior art pouches. The composite film 124 includes at least one odor barrier film layer and at least one foam layer, which are coextruded. Thus, manufacturing processes of the pouch can be simplified by reducing number of suppliers required for film, nonwoven and adhesive, and eliminating steps for laminating or heat sealing the layers, which in turn provides cost savings. The foam layer of the composite film is configured to have softness sufficient for skin contact to replace the nonwoven layer of prior art pouches. The foam layer can be configured to have a skin contact quality soft feel by using rubbery resins and fine foam cells. Preferably, the foam layer also provides sound absorbing characteristics.

Preferably, the composite film 124 is configured to have a thickness similar to the total thickness of the film/nonwoven construction or the film/adhesive/nonwoven construction of prior art ostomy pouches. For example, the composite film 124 has an overall thickness of about 10 mil to about 16 mil. The composite film 125 can also be configured to have thinner thicknesses, for example, about 7 mil, to provide a lower cost composite film which still has similar softness and film characteristics as the thicker composite films. In some embodiments, the first wall 116 and the second wall 118 can be formed of different composite films, or only one of the first and second walls 116, 118 can be formed of a composite film.

Figure 3:
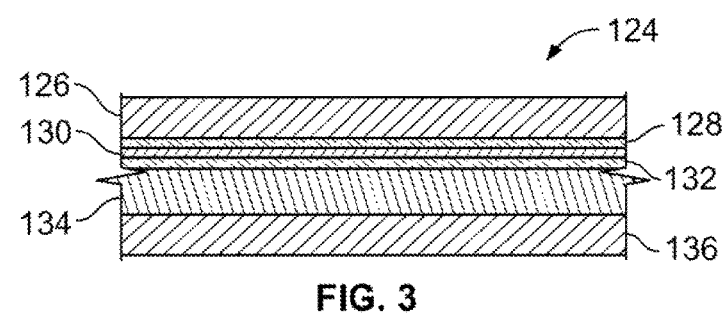
FIG. 3 is a cross-sectional illustration of a six-layer composite film according to an embodiment.

FIG. 3 is a cross-sectional illustration of an embodiment of the composite film 124. The composite film 124 has a six-layer construction including a seal layer 126, tie layers 128, 132, a barrier layer 130, and foam layers 134, 136. In this embodiment, the composite film 124 has the structure ABCBDE, where A represents the seal layer, B represents the tie layers, C represents the barrier layer, D represents an inner foam layer, and E represents an outer foam layer.

Figure 6:
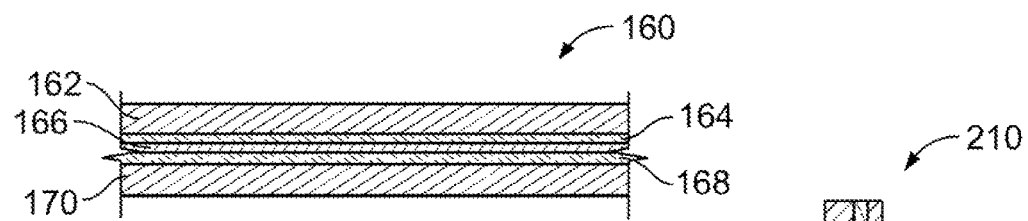
FIG. 6 is a cross-sectional illustration of a five-layer composite film according to an embodiment.

In other embodiments, the composite film can include more than six layers or less than six layers. For example, a composite film can have a five-layer construction including a barrier layer, two tie layers, a seal layer, and one foam layer (i.e. ABCBE). FIG. 6 is a cross-sectional illustration of a five-layer composite film embodiment including a seal layer 162, tie layers 164, 168, a barrier layer 166, and a foam layer 170. The composite film 160 has a seal/tie/barrier/tie/foam construction. Alternatively, a composite film can have a seven-layer construction including a barrier layer, two tie layers, a seal layer, and three foam layer (e.g. ABCBDDE).

The seal layer 126 is formed of a material having suitable heat sealability, such that the seal layers of the first and second walls 116, 118 can be heat sealed along their perimeter to form the pouch 112. Suitable materials for the seal layer 126 include ethylene based polymers, such as copolymers of ethylene with vinyl esters, e.g. EVA and EMA, ethylene alpha olefin copolymers (ethylene based plastomers), ethylene based elastomers (olefin block copolymers, OBC), and ethylene-propylene (EP) copolymers (PP-elastomer) and the blends thereof. Copolymers of ethylene with vinyl esters, such as ethylene vinyl acetate copolymer (EVA) and copolymers of ethylene methyl acrylate (EMA). Suitable EVA copolymers can contain about 5 wt. % to 35 wt. % vinyl acetate and more preferably, about 18 wt. % vinyl acetate, by weight of the copolymer. One such material is available from ExxonMobil as product Escorene® Ultra FL00218. Such a material has a melting point temperature of 86° C. and a Shore A hardness of about 91. EVA is known to exhibit the necessary characteristics for joining to another EVA member, as by heat sealing, to provide an air-tight, liquid-tight seal at the joint or seal. EVA materials can be blended to facilitate formation and film extrusion. For example, an EVA blend can have about 98 percent by weight (wt. %) EVA with about 2 wt. % anti-block and slip additives, in an EVA carrier. One suitable additive is available from A. Schulman Inc., as Polybatch® SAB-1982VA.

Suitable EMA copolymers can include about 5 wt. % to about 35 wt. % of the methyl acrylate and preferably about 15 wt. % to about 30 wt. % methyl acrylate. One such EMA copolymer is Lotryl® 18AM02 supplied by Arkema Inc. This copolymer has a melting point of 83° C. and specific gravity of 0.841. The EMA resins can also be blended with anti-block and slip additives in an EVA carrier. One suitable material for blending is the aforementioned Polybatch® SAB-1982VA. Such a blend can have, for example EMA at about 98 wt. %, with about 2 wt. % Polybatch® SAB-1982VA anti-block and slip additive.

Another suitable material is an ethylene alpha olefin copolymers (ethylene based plastomers). One such a material is Exact® 0203 resin, supplied by ExxonMobil Corporation, which has a specific gravity of about 0.88, a Shore A hardness of about 95, a melting point temperature of about 95° C., and specific gravity of about 0.902. Another suitable resin is ethylene based elastomers (olefin block copolymers, OBC). One such material is Infuse® 9107 supplied by Dow. This material has a specific gravity of about 0.866, a Shore A hardness of about 60 and a melting point of about 121° C. Still another suitable resin is an ethylene-propylene copolymer (PP-elastomer) resin. It has excellent compatibility with polypropylene (PP) and polyethylene (PE). One such material is available from Dow Chemical as Versify®2200. This resin has melting point of about 82° C., a Shore A hardness of 94 and a Shore D hardness of 42. It has a specific gravity of 0.878. PP-elastomers such as Vistamaxx® from Exxon, and Notio® from Mitsui are also suitable.

For example, a blend for seal layer 126 can have about 49 wt. % EVA copolymer (Escorene® Ultra FL00218), about 49% ethylene alpha olefin copolymer (Exact® 0203), and about 2 wt. % Polybatch® SAB-1982VA anti-block and slip additive. Another example for a blend for seal layer 126 can have about 49 wt. % EMA copolymer (Lotryl® 18AM02), about 49% OBC (Infuse® 9107), and about 2 wt. % Polybatch® SAB-1982VA anti-block and slip additive. Yet, another example for the seal layer 126 can have about 49 wt. % EMA copolymer (Lotryl® 18AM02), about 49% ethylene-propylene copolymer (Versify®2200), and about 2 wt. % Polybatch® SAB-1982VA anti-block and slip additive.

In addition to heat sealability, the seal layer 126 can also provide sound absorbing properties. In such an embodiment, the seal layer 126 can comprise a vinyl-bond rich triblock copolymer, such as Hybrar®, to enhance sound absorbing properties and mechanical properties of the composite film. For example, the seal layer 126 can be formed from a blend of a vinyl-bond rich SIS triblock copolymer (Hybrar® 5127), a PP-elastomer (Vistamaxx®), and an EMA (Lotryl® 20MA08).

On either side of the barrier layer 130 are the tie layers 128, 132. The tie layers facilitate adhesion of the barrier layer 130 to the remainder of the composite film structure. The seal layer 126 and the inner foam layer 134 are adjacent to the tie layers 128, 132, respectively. The tie layers 128, 132 can be formed of the same material or different materials. Suitable materials for the ties layers 128, 132 include maleated polyolefins, such as a maleated ethylene methyl acrylate copolymers having maleic anhydride present at about 0.3 wt. % and methyl acrylate present at about 20 wt. % of the resin. One such material is available from Arkema, Inc. as Lotader®4503.

In addition to the adhesion function, the tie layers 128, 132 can also provide sound absorbing properties. In such an embodiment, the tie layers 128, 132 can comprise a vinyl-bond rich triblock copolymer, such as Hybrar®, to enhance sound absorbing properties and mechanical properties of the composite film. For example, the tie layers 128, 132 can be formed from a blend of a vinyl-bond rich SIS block copolymer (Hybrar® 5127), a maleated LLDPE (Bynel® CXA41E710 supplied by DuPont), and an antioxidant, or can be formed from a blend of a vinyl-bond rich SEPS block copolymer (Hybrar® 7125) and a maleated LLDPE (Bynel® CXA41E710).

The barrier layer 130 can be formed from various materials having gas barrier properties, such as, but not limited to, polyvinylidene chloride, vinylidene copolymer, polyamide, and ethylene-vinyl alcohol copolymer. Preferably, the barrier layer 130 is formed from a non-chlorine containing polymer that is substantially impermeable to malodor causing compounds typically encountered in ostomy pouches. Such malodor causing compounds can include sulfur containing compounds and indoles. Suitable barrier layer materials include resins such as amorphous polyamide (nylon) resin, which can be modified by an anhydride-modified olefinic polymer or copolymer, or an epoxy modified olefin polymer or copolymer to decrease the rigidity of the barrier layer. For example, the barrier layer 130 can be formed from a blend of an amorphous polyamide, such as Selar® PA3426R, by DuPont Company, and a functionalized rubber blend or compound, such as Lotader® 4720.

The inner foam layer 134 and the outer foam layer 136 can be formulated from the same material or different materials. For example, the inner foam layer 134 can be formed from a polyolefin with a blowing agent and a color additive, and the outer foam layer 136 can be formed from the same polyolefin with a blowing agent, slip and antiblock agents, and a color additive. Ethylene based polymers, such as copolymers of ethylene with vinyl esters, e.g. EVA and EMA, ethylene alpha olefin copolymers (ethylene based plastomers), ethylene based elastomers (olefin block copolymers, OBC), and ethylene-propylene (EP) copolymers (PP-elastomer) and the blends thereof are suitable for the foam layers. One suitable material is an ethylene vinyl acetate (EVA) copolymer having a vinyl acetate content of about 5 wt. % to 35 wt. %, and preferably about 10 wt. % to about 30 wt. %. One such material is Escorene® FL00218, supplied by ExxonMobil Corporation. The material contains 18 wt. % vinyl acetate and has a melting point temperature of about 86° C. and a Shore A hardness of about 91. Suitable EMA copolymers can include about 5 wt. % to about 35 wt. % methyl acrylate and preferably about 10 wt. % to about 30 wt. % methyl acrylate. One such EMA copolymer is Lotryl® 18AM02 supplied by Arkema Inc. This copolymer has a melting point of 83° C. and specific gravity of 0.841.

Another suitable material is ethylene alpha olefin copolymers (ethylene based plastomers). One such material is Exact® 0203 resin, supplied by ExxonMobil Corporation, which has a specific gravity of about 0.88, a Shore A hardness of about 95, a melting point temperature of about 95° C., and specific gravity of about 0.902. Another suitable resin is ethylene based elastomers (olefin block copolymers, OBC). One such material is Infuse® 9107 supplied by Dow. This material has a specific gravity of about 0.866, a Shore A hardness of about 60 and a melting point of about 121° C. Still another suitable resin is an ethylene-propylene copolymer (PP-elastomer) resin. It has excellent compatibility with polypropylene (PP) and polyethylene (PE). One such material is available from Dow Chemical as Versify® 2200. This resin has melting point of about 82° C., a Shore A hardness of 94, a Shore D hardness of 42, and a specific gravity of 0.878.

Preferably, the foam layers 134, 136 also provide at least some sound absorbing properties. In such an embodiment, each of the foam layers 134, 136 comprises a vinyl-bond rich triblock copolymer, such as Hybrar® from Kuraray Co. Ltd., to enhance mechanical properties and sound absorbing properties of the composite film. For example, each of the foam layers can be formed from a blend comprising a vinyl-bond rich SIS block copolymer, e.g. Hybrar® 5125 and 5127, or a vinyl-bond rich SEPS block copolymer, e.g. Hybrar® 7125, or a vinyl-bond rich SEEPS block copolymer, e.g. Hybrar® 7311. The vinyl-bond rich triblock copolymers can be used alone with foaming agent or blended with other polyolefins, such as EMA (e.g. Lotryl® 20MA08), to form the foam layers 134, 136. The foam layers may also include other additive ingredients, such as a processing aid (e.g. Polyone® FDM 55802 from PolyOne).

In one embodiment, the six-layer composite film 124 has a total thickness of about 280 µm (11 mil), in which the seal layer 126 has a thickness of about 64 µm, each of the tie layers 128, 132 has a thickness of about 4 µm, the barrier layer 130 has a thickness of about 4 µm, the inner foam layer 134 has a thickness of about 140 µm, and the outer foam layer 136 has a thickness of about 64 µm.

In this embodiment, the seal layer 126 is formed a blend comprising about 49 wt. % of EVA copolymer (Escorene® FL00218), about 49 wt. % of PP-elastomers (Vistamaxx® 3980FL), and about 2 wt. % of a slip and antiblock agent (Polybatch® SAB-1982VA). Each of the tie layers 128, 132 is formed from a blend comprising about 80 wt. % EMA (Lotryl® 18MA02) and about 20 wt. % MAH grafted LLDPE (Bynel® CXA41E710). The barrier layer is formed from a blend comprising about 85 wt. % amorphous polyamide (Selar® PA3426R) and 15 wt. % functionalized rubber blend (Lotader® 4720). The inner foam layer 134 is formed from a blend comprising about 45 wt. % of EVA copolymer (Escorene® FL00218), about 45 wt. % of PP-elastomers (Vistamaxx® 3980FL), about 8 wt. % of color masterbatch, and about 2 wt. % of blowing agent (Safoam® FP-40 from Reedy International). The outer foam layer 136 is formed from a blend comprising about 48 wt. % of EVA copolymer (Escorene® FL00218), about 48 wt. % of PP-elastomers (Vistamaxx® 3980FL), about 2 wt. % of blowing agent (Safoam® FP-40), and about 2 wt. % of slip and antiblock agent (Polybatch® SAB-1982VA). The foam layers 134, 136, particularly the outer foam layer 136, include fine foam cells for soft skin touch feel. Further, the slip agent is added to the blend for the outer foam layer 136 to improve the smooth sleek feel of the foam.

Preferably, the foam layers provide sound absorbing properties in addition to a smooth soft feel for improved comfort for wearers. Thus, at least one foam layer comprises a vinyl-bond rich triblock copolymer such as a vinyl-bond rich SIS block copolymer, e.g. Hybrar® 5125 and 5127, or a vinyl-bond rich SEPS block copolymer, e.g. Hybrar® 7125, or a vinyl-bond rich SEEPS block copolymer, e.g. Hybrar® 7311.

In one embodiment, the six-layer composite film 124 has a total thickness of about 288 µm (11.3 mil), in which the seal layer 126 has a thickness of about 20 µm, each of the tie layers 128, 132 has a thickness of about 3 µm, the barrier layer 130 has a thickness of about 4 µm, the inner foam layer 134 has a thickness of about 238 µm, and the outer foam layer 136 has a thickness of about 20 µm.

In this embodiment, the seal layer 126 is formed from a blend comprising about 49 wt. % of EVA copolymer (Escorene® FL00218), about 49 wt. % of PP-elastomers (Vistamaxx® 3980FL), and about 2 wt. % of a slip and antiblock agent (Polybatch® SAB-1982VA). Each of the tie layers 128, 132 is formed from a blend comprising about 80 wt. % EMA (Lotryl® 18MA02) and about 20 wt. % MAH grafted LLDPE (Bynel® CXA41E710). The barrier layer 130 is formed from a blend comprising about 85 wt. % amorphous polyamide (Selar® PA3426R) and 15 wt. % functionalized rubber blend (Lotader® 4720). The inner foam layer 134 is formed from a blend comprising about 47 wt. % of vinyl-bond rich SEPS block copolymer (Hybrar® 7125), about 47 wt. % of EMA (Lotryl® 20MA08), about 4 wt. % of color masterbatch, and about 2 wt. % of blowing agent (Safoam® FP-20). The outer foam layer 136 is formed from a blend comprising about 48 wt. % of vinyl-bond rich SEPS block copolymer (Hybrar® 7125), about 48 wt. % of EMA (Lotryl® 20MA08), about 2 wt. % of blowing agent (Safoam® FP-20), and about 2 wt. % of slip and antiblock agent (Polybatch® SAB-1982VA). Preferably, the foam layers 134, 136 include fine foam cells for soft smooth feel, and open cell structure to maximize sound absorbing properties of the foam layers. Further, the slip agent is added to the blend for the outer foam layer 136 for improved smooth sleek feel of the foam.

In another embodiment, the six-layer composite film 124 has a total thickness of about 288 µm (11.3 mil), in which the seal layer 126 has a thickness of about 20 µm, each of the tie layers 128, 132 has a thickness of about 3 µm, the barrier layer 130 has a thickness of about 40 µm, the inner foam layer 134 has a thickness of about 202 µm, and the outer foam layer 136 has a thickness of about 20 µm. In this embodiment, the barrier layer 130 is formed from a low melting point nylon, and thus, a vinyl-bond rich SIS block copolymer (Hybrar® 5125 or 5127), which is thermally not as stable as has a lower melting point than the vinyl-bond rich SEPS block copolymer (Hybrar® 7125) or SEEPS block copolymer (Hybrar® 7311), can be used for the foam layers 134, 136. In the previously described embodiment, the amorphous polyamide (Selar® PA3426R) used for the barrier layer has a relatively high melt flow temperature, thus requires a relatively high processing temperature. Therefore, the vinyl-bond rich SEPS or SEEPS block copolymer, which is more heat stable than the vinyl-bond rich SIS block copolymer, was selected for the foam layers. The vinyl-bond rich SIS block copolymers can provide additional cost benefits and improved sound absorbing properties in some embodiments.

In this embodiment, the seal layer 126 is formed from a blend comprising about 59 wt. % of EMA (Lotryl® 20MA08), about 39 wt. % of PP-elastomers (Vistamaxx® 3980FL), and about 2 wt. % of a slip and antiblock agent (Polybatch® SAB-1982VA). Each of the tie layers 128, 132 is formed from a blend comprising about 80 wt. % EMA (Lotryl® 20MA08) and about 20 wt. % MAH grafted LLDPE (Bynel® CXA41E710). The barrier layer 130 is formed from a blend comprising about 85 wt. % low melting point nylon (Grilon® BM13 from EMS-Grivory) and 15 wt. % functionalized rubber blend (Lotader® 4720). The inner foam layer 134 is formed from a blend comprising about 46.5 wt. % of vinyl-bond rich SIS block copolymer (Hybrar® 5127), about 46.5 wt. % of EMA (Lotryl® 20MA08), about 5 wt. % of color masterbatch, and about 2 wt. % of blowing agent (Safoam® FP-20). The outer foam layer 136 is formed from a blend comprising about 48 wt. % of vinyl-bond rich SIS block copolymer (Hybrar® 5127), about 48 wt. % of EMA (Lotryl® 20MA08), about 2 wt. % of blowing agent (Safoam® FP-20), and about 2 wt. % of slip and antiblock agent (Polybatch® SAB-1982VA). Preferably, the foam layers 134, 136 include fine foam cells for soft smooth feel, and open cell structure to maximize sound absorbing properties of the foam layers. Further, the slip agent is added to the blend for the outer foam layer 136 for an improved smooth sleek feel of the foam.

In some embodiments, a composite film includes at least one layer comprising a filler to provide improved sound absorbing or sound deadening properties. Fillers having a platelet shape, such as mica and talc, are preferred. For example, a composite film having improved sound absorbing properties can include at least one sound absorbing foam layer comprising a vinyl-bond rich triblock copolymer and at least one other layer comprising a filler, such as mica, barium sulfate, and/or talc.

In one embodiment, a six-layer composite film 124 (FIG. 3) includes a seal layer comprising a filler. The composite film has a total thickness of about 288 μm (11.3 mil) including a seal layer 126 having a thickness of about 25 μm, two tie layers 128, 132, each of which having a thickness of about 4 μm, a barrier layer 130 having a thickness of about 4 μm, an inner foam layer 134 having a thickness of about 166 μm, and an outer foam layer 136 having a thickness of about 85 μm. The seal layer 126 is formed from a polymer blend comprising about 33.3 wt. % of a EMA/mica blend (the EMA/mica blend includes about 50 wt. % mica (Suzorite® 60S from Imerys Pigments) and about 50 wt. % EMA (Lotryl® 20MA08)), about 25 wt. % of EMA (Lotryl® 20MA08), about 40 wt. % of PP-elastomers (Vistamaxx® 3980FL), and about 1.7 wt. % of a slip and antiblock agent (Polybatch® SAB-1982VA). Each of the tie layers 128, 132 is formed from a blend comprising about 80 wt. % EMA (Lotryl® 18MA02) and about 20 wt. % MAH grafted LLDPE (Bynel® CXA41E710). The barrier layer 130 is formed from a blend comprising about 85 wt. % amorphous polyamide (Selar® PA3426R) and about 15 wt. % functionalized rubber blend (Lotader® 4720). The inner foam layer 134 is formed from a blend comprising about 55 wt. % of vinyl-bond rich SEPS block copolymer (Hybrar® 7125), about 31 wt. % of EMA (EMAC® 2207 from West Lake), about 11 wt. % of color masterbatch, and about 3 wt. % of blowing agent (Expancel® 950MB80 from Akzo). The outer foam layer 136 is formed from a blend comprising about 52 wt. % of vinyl-bond rich SEPS block copolymer (Hybrar® 7125), about 43 wt. % of EMA (Lotryl® 20MA08), about 3 wt. % of blowing agent (Expancel® 950MB80), and about 2 wt. % of slip and antiblock agent (Polybatch® SAB-1982VA).

Figure 7:
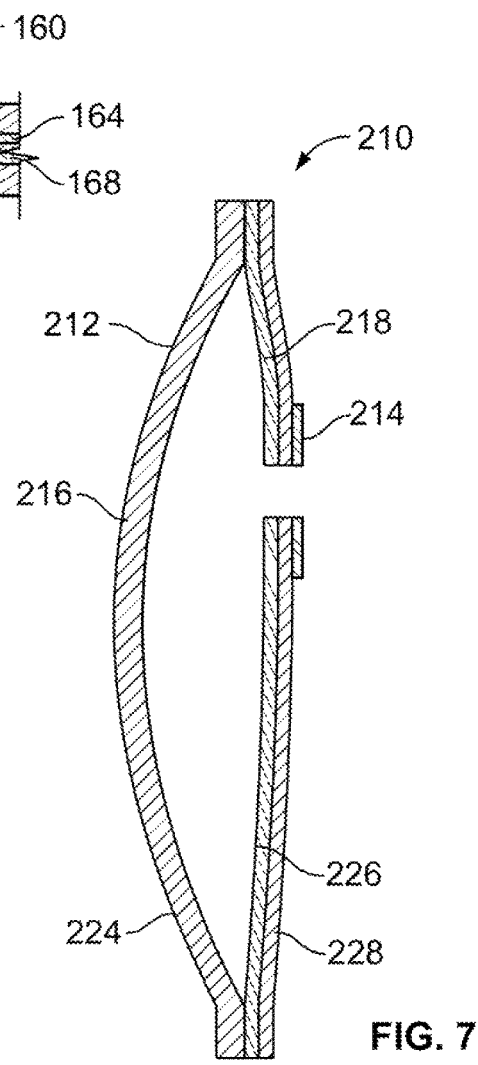
FIG. 7 is a cross-sectional illustration of an ostomy pouch according to another embodiment of the present disclosure.

FIG. 7 is a cross-sectional illustration of a one-piece ostomy pouch 210 according to another embodiment. The ostomy pouch 210 is similarly configured as the ostomy pouch 110 of FIG. 2, and generally includes a pouch 212 and a skin barrier 214. In this embodiment, a first wall 216 is formed of a composite film 224, and a second wall 218 is formed of a film 226. Further, the ostomy pouch 210 includes a nonwoven layer 228 attached to the second wall 218 to accommodate users who desire characteristics of a nonwoven comfort panel, for example, breathability.

Figure 4:
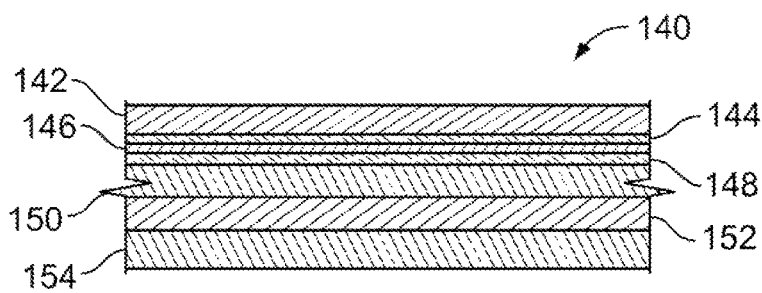
FIG. 4 is a cross-sectional illustration a seven-layer composite film according to an embodiment.

The composite film 224 includes at least one sound absorbing foam layer comprising a vinyl-bond rich triblock copolymer such as a vinyl-bond rich SIS block copolymer, e.g. Hybrar® 5125 and 5127, or a vinyl-bond rich SEPS block copolymer, e.g. Hybrar® 7125, or a vinyl-bond rich SEEPS block copolymer, e.g. Hybrar® 7311. The composite film 224 can have any of the multilayer composite constructions discussed in this disclosure. For example, the composite film 224 can have a six-layer construction including a seal layer, two tie layers, a barrier layer, and two foam layers, as shown in FIG. 3. Alternatively, the composite film 224 can have a five-layer construction as shown in FIG. 6 or a seven-layer construction as shown in FIG. 4.

The second wall 218 can be formed of a suitable monolayer or multilayer film, such as a composite film including at least one sound absorbing foam layer comprising a vinyl-bond rich triblock copolymer. For example, the film 226 can be the same composite film as the composite film 224 or a different composite film. In one embodiment, the composite film 224 and the film 226 are the same composite film having a six-layer construction of FIG. 3, which includes two foam layers 134, 136 comprising a vinyl-bond rich triblock copolymer. In another embodiment, the film 226 is a different composite film than the composite film 224. For example, the film 226 can be a thinner composite film than the composite film 224. For example, the composite film 224 can have a thickness of about 11 mil, while the film 226 is a composite film having a thickness of about 7 mil.

Alternatively, the film 226 can be a suitable polymeric film, which does not include a foam layer. The film 226 can be a single layer film or a multilayer film. Preferably, the multilayer film includes at least one odor barrier layer. For example, the film 226 can be a six-layer film having a thickness of about 2.24 mil (57 μm) and a seal layer/tie layer/barrier layer/tie layer/inner layer/seal layer construction. In another example, the film 226 can be a seven-layer film having a seal layer/inner layer/tie layer/barrier layer/tie layer/inner layer/seal layer construction. In some embodiments, the multilayer film for the second wall 218 includes at least one layer comprising a vinyl-bond rich triblock copolymer.

Although the embodiments of FIGS. 2 and 7 are a one-piece ostomy appliance with a closed-end pouch, the above discussed multilayer composite films can be used to make other types of ostomy appliances, such as two-piece ostomy appliances and drainable ostomy pouches.

Examples and Test Results

Three composite film samples and a control laminate were prepared and tested for their mechanical and sound absorbing properties. Each of the composite film samples had a total thickness of about 288 μm (11.3 mil) and a seven-layer construction (seal layer/tie layer/barrier layer/tie layer/foam layer/foam layer/foam layer). Each of the foam layers included vinyl-bond rich SEPS block copolymer (Hybrar® 7125) for sound absorbing properties. The control laminate, which is currently used in some known ostomy pouches, had a total thickness of about 11.3 mil including a PE nonwoven layer, an adhesive layer, and a multilayer barrier film.

(Lotryl® 20MA08), about 2 wt. % of blowing agent (Safoam® FP-20), and about 2 wt. % of slip and antiblock agent (Polybatch® SAB-1982VA). Thus, the composite film 140 of Sample X3299 has a total thickness of about 288 μm (11.3 mil).

TABLE 1

Composite Film Samples and Control Laminate

| Sample Code | Foam 1 | Foam 2 | Foam 3 | Tie 1 | Barrier | Tie 2 | Seal |
|---|---|---|---|---|---|---|---|
| X3299 | 85 μm 50% Hybrar® 7125 + 46% Lotryl® 20MA08 + 2% Safoam® FP-20 + 2% Polybatch® SAB-1982VA | 83 μm 65% Hybrar® 7125 + 34% EMAC® 2207 + 1% Safoam® FP-20 | 83 μm 65% Hybrar® 7125 + 34% EMAC® 2207 + 1% Safoam® FP-20 | 4 μm 80% Lotryl® 18MA02 + 20% Bynel® CXA41E710 | 4 μm 85% Selar® PA3426R + 15% Lotader® 4720 | 4 μm same as Tie 1 | 25 μm 50% Lotryl® 20MA08 + 48% Vistamaxx® 3980FL + 2% Polybatch® SAB-1982VA |
| X3300 | 85 μm 50% Hybrar® 7125 + 46% Lotryl® 20MA08 + 2% Safoam® FPE-20 + 2% Polybatch® SAB-1982VA | 83 μm 65% Hybrar® 7125 + 34% EMAC® 2207 + 1% Safoam® FPE-20 | 83 μm 65% Hybrar® 7125 + 34% EMAC® 2207 + 1% Safoam® FPE-20 | 4 μm 80% Lotryl® 18MA02 + 20% Bynel® CXA41E710 | 4 μm 85% Selar® PA3426R + 15% Lotader® 4720 | 4 μm same as Tie 1 | 25 μm 50% Lotryl® 20MA08 + 48% Vistamaxx® 3980FL + 2% Polybatch® SAB-1982VA |
| X3301 | 85 μm 50% Hybrar® 7125 + 46% Lotryl® 20MA08 + 2% Expancel® 950MB80 + 2% Polybatch® SAB-1982VA | 83 μm 65% Hybrar® 7125 + 34% EMAC® 2207 + 1% Expancel® 950MB80 | 83 μm 65% Hybrar® 7125 + 34% EMAC® 2207 + 1% Expancel® 950MB80 | 4 μm 80% Lotryl® 18MA02 + 20% Bynel® CXA41E710 | 4 μm 85% Selar® PA3426R + 15% Lotader® 4720 | 4 μm same as Tie 1 | 25 μm 50% Lotryl® 20MA08 + 48% Vistamaxx® 3980FL + 2% Polybatch® SAB-1982VA |

| | Nonwoven | Adhesive | 57 μm (2.24 mil) 6-layer film | | | | |
|---|---|---|---|---|---|---|---|
| | | | Seal | Inner | Tie 1 | Barrier | Tie 2 | Seal |
| Control | 203.2 μm (8 mil) PE nonwoven | 28 μm (1.1 mil) adhesive | 97.5% Escorene® FL00218 + 2.5% Polybatch® SAB-1982VA | 87%-89.5% Escorene® FL00218 + 10.5%-13% Schulman® T92030 Beige | 80% Lotryl® 18MA02 + 20% Bynel® CXA-41E710 | 85% Selar® PA3426R + 15% Lotader® 4720 | same as Tie 1 | 97.5% Escorene® FL00218 + 2.5% Polybatch® SAB-1982VA |

As summarized in Table 1, Sample X3299 is a seven-layer composite film 140 (FIG. 4) having a foam layer 1/foam layer 2/foam layer 3/tie layer 1/barrier layer/tie layer 2/seal layer construction. The seal layer 142 has a thickness of about 25 μm, and is formed of a blend comprising about 50 wt. % of EMA (Lotryl® 20MA08), about 48 wt. % of PP-elastomers (Vistamaxx® 3980FL), and about 2 wt. % of a slip and antiblock agent (Polybatch® SAB-1982VA). Each of the tie layer 1 (148) and tie layer 2 (144) has a thickness of about 4 μm, and is formed from a blend comprising about 80 wt. % EMA (Lotryl® 18MA02) and about 20 wt. % MAH grafted LLDPE (Bynel® CXA41E710). The barrier layer 146 has a thickness of about 4 μm, and is formed from a blend comprising about 85 wt. % amorphous polyamide (Selar® PA3426R) and about 15 wt. % functionalized rubber blend (Lotader® 4720). Each of the foam layer 2 (152) and the foam layer 3 (150) has a thickness of about 83 μm, and is formed from a blend comprising about 65 wt. % of vinyl-bond rich SEPS block copolymer (Hybrar® 7125), about 34 wt. % of EMA (EMAC® 2207), and about 1 wt. % of blowing agent (Safoam® FP-20). The foam layer 1 (154) has a thickness of about 85 μm, and is formed from a blend comprising about 50 wt. % of vinyl-bond rich SEPS block copolymer (Hybrar® 7125), about 46 wt. % of EMA Sample X3300 is also a seven-layer composite film 140 having the same layer construction as Sample X3299, which is illustrated in FIG. 4. The seal layer 142 has a thickness of about 25 μm, and is formed from a blend comprising about 50 wt. % of EMA (Lotryl® 20MA08), about 48 wt. % of PP-elastomers (Vistamaxx® 3980FL), and about 2 wt. % of a slip and antiblock agent (Polybatch® SAB-1982VA). Each of the tie layer 1 (148) and tie layer 2 (144) has a thickness of about 4 μm, and is formed from a blend comprising about 80 wt. % EMA (Lotryl® 18MA02) and about 20 wt. % MAH grafted LLDPE (Bynel® CXA41E710). The barrier layer 146 has a thickness of about 4 μm, and is formed from a blend comprising about 85 wt. % amorphous polyamide (Selar® PA3426R) and about 15 wt. % functionalized rubber blend (Lotader® 4720). Each of the foam layer 2 (152) and the foam layer 3 (150) has a thickness of about 83 μm, and is formed from a blend comprising about 65 wt. % of vinyl-bond rich SEPS block copolymer (Hybrar® 7125), about 34 wt. % of EMA (EMAC® 2207), and about 1 wt. % of blowing agent (Safoam® FPE-20). The foam layer 1 (154) has a thickness of about 85 μm, and is formed from a blend comprising about 50 wt. % of vinyl-bond rich SEPS block copolymer (Hybrar® 7125), about 46 wt. % of EMA (Lotryl® 20MA08), about 2 wt. % of blowing agent (Safoam® FPE-20), and about 2 wt. % of slip and antiblock agent (Polybatch® SAB-1982VA). Thus, the composite film 140 of Sample X3300 has a total thickness of about 288 μm (11.3 mil).

Sample X3301 is also a seven-layer composite film 140 having the same layer construction as Sample X3299, which is illustrated in FIG. 4. The seal layer 142 has a thickness of about 25 μm, and is formed from a blend comprising about 50 wt. % of EMA (Lotryl® 20MA08), about 48 wt. % of PP-elastomers (Vistamaxx® 3980FL), and about 2 wt. % of a slip and antiblock agent (Polybatch® SAB-1982VA). Each of the tie layer 1 (148) and tie layer 2 (144) has a thickness of about 4 μm, and is formed from a blend comprising about 80 wt. % EMA (Lotryl® 18MA02) and about 20 wt. % MAH grafted LLDPE (Bynel® CXA41E710). The barrier layer 146 has a thickness of about 4 μm, and is formed from a blend comprising about 85 wt. % amorphous polyamide (Selar® PA3426R) and about 15 wt. % functionalized rubber blend (Lotader® 4720). Each of the foam layer 2 (152) and the foam layer 3 (150) has a thickness of about 83 μm, and is formed from a blend comprising about 65 wt. % of vinyl-bond rich SEPS block copolymer (Hybrar® 7125), about 34 wt. % of EMA (EMAC® 2207), and about 1 wt. % of blowing agent (Expancel® 950MB80 from Akzo). The foam layer 1 (154) has a thickness of about 85 μm, and is formed from a blend comprising about 50 wt. % of vinyl-bond rich SEPS block copolymer (Hybrar® 7125), about 46 wt. % of EMA (Lotryl® 20MA08), about 2 wt. % of blowing agent (Expancel® 950MB80), and about 2 wt. % of slip and antiblock agent (Polybatch® SAB-1982VA). Thus, the composite film 140 of Sample X3301 has a total thickness of about 288 μm (11.3 mil).

The layers of Samples X3299, X3300, and X3301 were coextruded to form the composite film 140. Each layer was extruded using a separate extruder with appropriate settings for the particular polymer blend.

The control laminate had a thickness of about 11.3 mil, and included a PE nonwoven laminated to a six-layer odor barrier film with an adhesive between them. The six-layer odor barrier film had a thickness of about 2.24 mil (57 μm), and a seal layer/tie layer/barrier layer/tie layer/inner layer/seal layer construction. Each of the seal layers was formed from a blend of about 97.5% wt. EVA copolymer (Escorene® FL00218 available from ExxonMobil Corporation) and about 2.5 wt. % anti-block/slip additive (Polybatch® SAB1982VA available from Schulman Inc.) Each of the tie layers was formed from a blend of about 80 wt. % EMA (Lotryl® 18MA02) and about 20 wt. % MAH grafted LLDPE (Bynel® CXA41E710.) The barrier layer was formed from a blend of about 85 wt. % of an amorphous polyamide (Selar® PA3426R) and about 15 wt. % functionalized rubber blend (Lotader® 4720.) The inner layer was formed from a blend of about 87 wt. %-89.5 wt. % EVA copolymer (Escorene® FL00218) and about 10.5 wt. %-13 wt. % Schulman® T92030 Beige.

Mechanical properties of the sample composites and the control laminate were evaluated, and their data is summarized in Table 2.

TABLE 2

Mechanical Properties of Samples

|  | X3299 | X3300 | X3301 | Control |
|---|---|---|---|---|
| Actual Total Thickness (μm) | 280 | 288 | 294 | 280 |

TABLE 2-continued

Mechanical Properties of Samples

|  |  | X3299 | X3300 | X3301 | Control |
|---|---|---|---|---|---|
| Elmendorf Tear at 800 mm (mN) | MD | 23154 | 24036 | 14058 | — |
|  | CD | 13327 | 15872 | 9847 | — |
| Elmendorf Tear at 800 mm (mN/mil) | MD | 2049 | 2127 | 1244 | — |
|  | CD | 1179 | 1405 | 871 | — |
| Elmendorf Tear at 800 mm (gf/mil) | MD | 209 | 217 | 127 | — |
|  | CD | 120 | 143 | 89 | — |
| Tensile Strength (N/mm$^2$) | MD | 6.9 | 6.6 | 4.3 | 6.9 |
|  | CD | 6.7 | 6.5 | 4.0 | 2.8 |
| Tensile Strength (psi) | MD | 1000 | 951 | 626 | 1001 |
|  | CD | 965 | 937 | 586 | 405 |
| Tensile Yield (N/mm$^2$) | MD | 2.8 | 2.1 | 2.3 | 3.6 |
|  | CD | 2.3 | 2.2 | 1.7 | 2.5 |
| Tensile Yield (psi) | MD | 412 | 308 | 333 | 522 |
|  | CD | 327 | 312 | 245 | 356 |
| Elongation at Break (%) | MD | 628 | 746 | 532 | 254 |
|  | CD | 746 | 745 | 679 | 403 |
| Elongation at Yield (%) | MD | 42.9 | 37.9 | 32.4 | 137 |
|  | CD | 33.4 | 35.1 | 37.3 | 86 |
| Modulus (N/mm$^2$) | MD | 46.7 | 34.2 | 36.7 | 33.8 |
|  | CD | 37.8 | 32.8 | 26.5 | 26.2 |
| Modulus (ksi) | MD | 6.8 | 5.0 | 5.3 | 4.9 |
|  | CD | 5.5 | 4.8 | 3.8 | 3.8 |

The modulus data as shown in Table 2 indicate that Samples X3299, X3300, and X3301 have similar softness as the control laminate. The tensile strength data in machine direction (MD) and cross direction (CD) indicates that the control laminate has more anisotropicity. The elongation at break data indicates that Samples X3299, X3300, and X3301 are more ductile than the control laminate. Further, Samples X3299, X3300, and X3301 have good Elmendorf tear strength. Overall, the data indicates that Samples X3299, X3300, and X3301 have suitable mechanical properties for ostomy pouches.

Samples X3299, X3300, and X3301 and the control laminate were tested according to ASTM E2611-09 (Standard Test Method for Measurement of Normal Incidence Sound Transmission of Acoustical Materials Based on the Transfer Matrix Method) using Bruel & Kjaer Sound Impedance Tube Kit-Type 4206T. In this test, a sound source (e.g. loudspeaker) is mounted at one end of an impedance tube, and the sample is placed in a holder in the tube at a distance away from the sound source. The loudspeaker generates broadband, stationary random sound waves that propagate as plane waves. The plane waves hit the sample with part of the waves reflected back into the source tube, part absorbed by the laminate sample, and part passing through the sample to a receiving tube. By measuring the sound pressure at four fixed locations (two in the source tube and two in the receiving tube) and calculating the complex transfer function using a four-channel digital frequency analyzer, the transmission loss of the laminate sample is determined.

Figure 5:
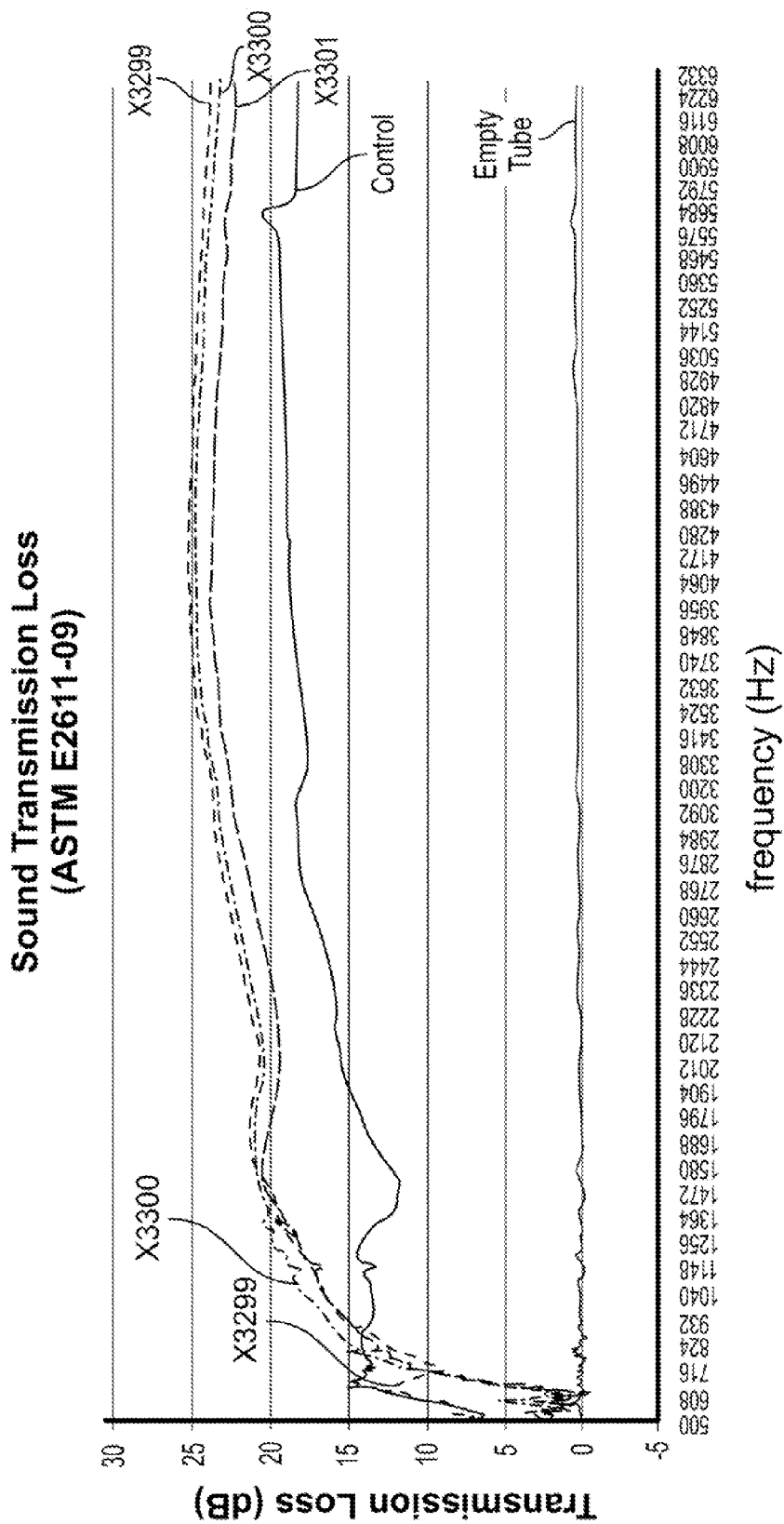
FIG. 5 is a graph showing sound transmission loss data for composite film samples.

The sound tube transmission loss test data for laminate samples are plotted and shown in FIG. 5. Transmission loss expressed in decibel (dB) shows the degree of sound reduced or absorbed by the samples. The most audible range of human hearing is between about 1,000 Hz to 4,000 Hz. As shown in FIG. 5, Samples X3299, X3300, and X3301 have significantly better sound reduction/absorption properties than the control laminate. For example, Samples X3299 and X3300 provided more sound reduction than the control laminated by more than about 6 dB at around 3,500-4,000 Hz frequencies. In ostomy applications, an improvement in the sound transmission loss of about 6 dB represents a significant reduction of embarrassing flatus gas noise.

Figure 8:
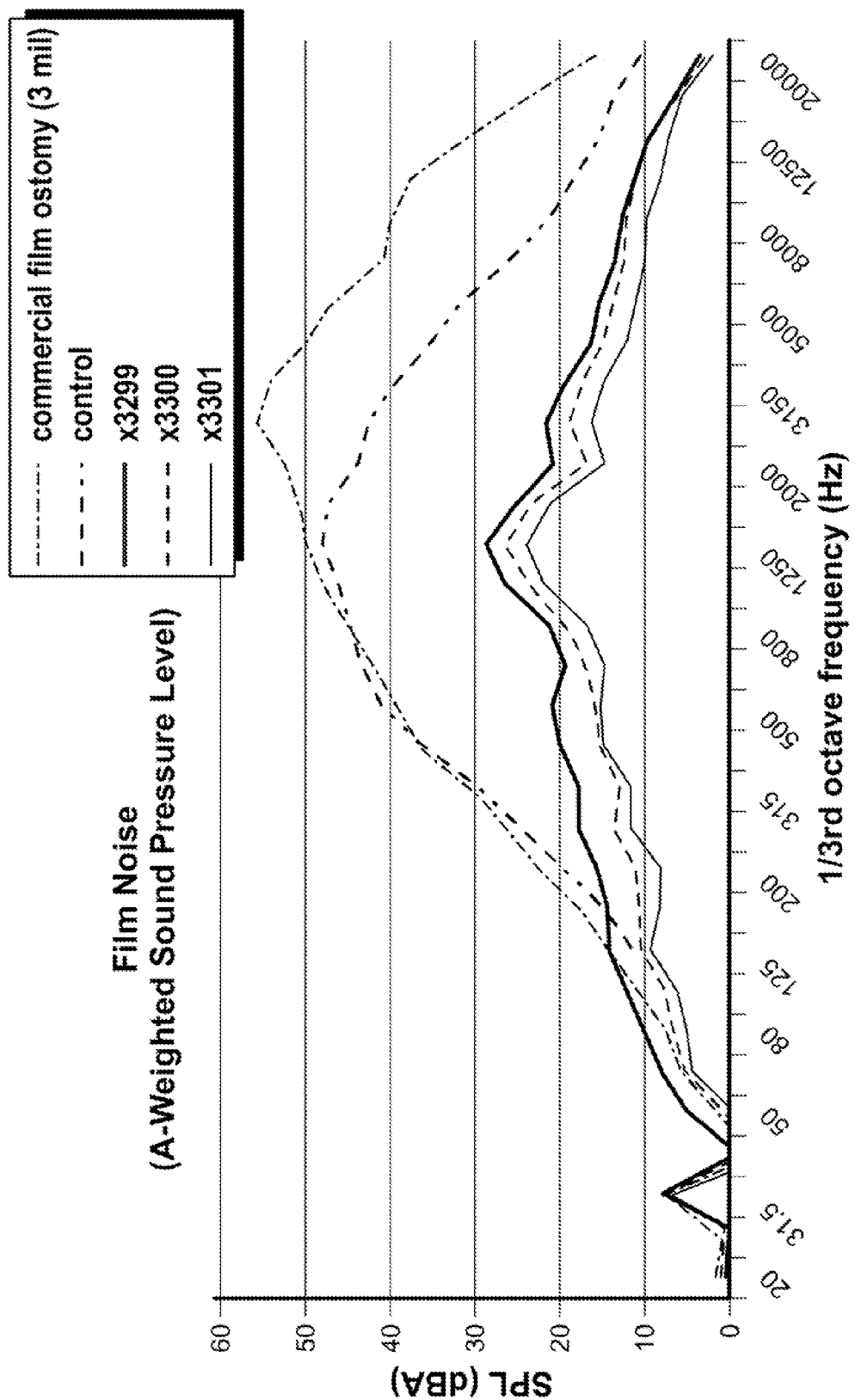
FIG. 8 is a graph showing film noise data in a-weighted sound pressure level for composite film samples.
Figure 9:
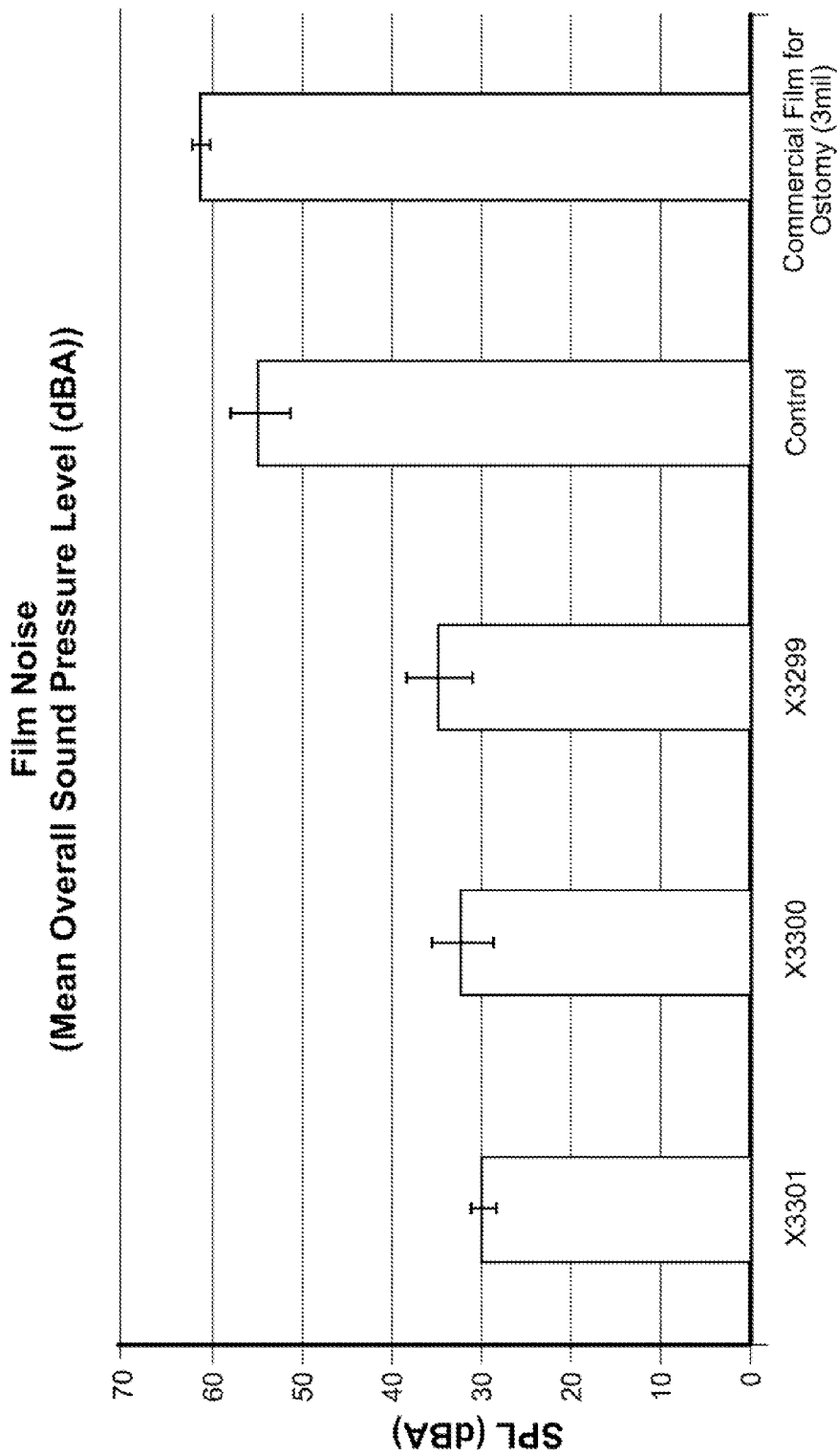
FIG. 9 is a graph showing film noise data in mean overall sound pressure level for composite film samples.

In addition to the sound absorbing properties, the laminate samples were also evaluated for film noise properties. The film noise properties are different than the sound absorbing properties in that the sound absorbing properties are indicative of sample's ability for reducing flatus noise, whereas the film noise properties are indicative of a level of noise produced by the sample itself, for example, crackling noise made by the sample. The film noise of the laminate samples were measured and plotted in FIGS. 8 and 9. FIG. 8 is a graph of a-weighted sound pressure level, and FIG. 9 is a graph of mean overall sound pressure level of the laminate samples, the control sample and a commercial film for ostomy pouch. The commercial film, which was a multilayer film including a barrier layer comprising vinylidene chloride-methyl acrylate copolymer, had a thickness of 3 mil. As can be seen in FIGS. 8 and 9, Samples X3299, X3300, and X3301 have significantly lower sound pressure levels than the control laminate and the commercial film. Thus, in addition to providing superior sound absorbing properties, the laminate samples also make less noise than the control laminate and the commercial film. That is, ostomy pouches made using the laminate samples can reduce flatus gas noise better, and are also quieter than those made using the control laminate or the commercial film.

Preferably, a composite film also includes at least one layer comprising a filler, such as talc, barium sulfate and/or mica, to further enhance sound absorbing properties. Two-layer laminate samples including a layer comprising barium sulfate or talc (Sample 302-2 and Sample 303-3) were prepared and evaluated for their sound absorbing properties. A two-layer control sample was also prepared. The compositions of the two-layer laminate samples and the control sample are summarized in Table 3.

TABLE 3

| | Laminate Samples and Control Sample | |
|---|---|---|
| | First Layer (1 mil) | Second Layer (2 mil) |
| Control | 50.0 wt. % of Lotryl ® 20MA08 + 48.0 wt. % Vistamaxx ® 3980FL + 2.0 wt. % Polybatch ® SAB-1982VA | 60 wt. % Hybrar ® 5125 + 38 wt. % Lotryl ® 20MA08 + 2 wt. % Polybatch ® SAB-1982VA |
| Sample 302-2 | 20.0 wt. % of Lotryl ® 20MA08 + 48.0 wt. % Vistamaxx ® 3980FL + 30.0 wt. % Huberbrite ® HB1 + 2.0 wt. % Polybatch ® SAB-1982VA | 60 wt. % Hybrar ® 5125 + 38 wt. % Lotryl ® 20MA08 + 2 wt. % Polybatch ® SAB-1982VA |
| Sample 302-3 | 20.0 wt. % of Lotryl ® 20MA08 + 48.0 wt. % Vistamaxx ® 3980FL + 30.0 wt. % Luzenac ® HAR T-84 + 2.0 wt. % Polybatch ® SAB-1982VA | 60 wt. % Hybrar ® 5125 + 38 wt. % Lotryl ® 20MA08 + 2 wt. % Polybatch ® SAB-1982VA |

Each of the samples (Sample 302-2 and Sample 303-3) and the control sample had a total thickness of about 3 mil, and included a first layer having a thickness of about 1 mil and a second layer having a thickness of 2 mil. The second layer of Sample 302-2, Sample 303-3, and the control sample was formed of the same film comprising about 60 wt. % of a vinyl-bond rich SIS block copolymer (Hybrar® 5125), about 38 wt. % of EMA (Lotryl® 20MA08), and about 2 wt. % of slip and antiblock agent (Polybatch® SAB-1982VA). The first layer of Sample 302-2 comprised about 20.0 wt. % of EMA (Lotryl® 20MA08), about 48.0 wt. % of PP-elastomers (Vistamaxx® 3980FL), about 30.0 wt. % barium sulfate (Huberbrite® HB1 from Huber), and about 2.0 wt. % of slip and antiblock agent (Polybatch® SAB-1982VA). The first layer of Sample 302-3 comprised about 20.0 wt. % of EMA (Lotryl® 20MA08), about 48.0 wt. % of PP-elastomers (Vistamaxx® 3980FL), about 30.0 wt. % talc (Luzenac® HAR T-84 from Imerys), and about 2.0 wt. % of slip and antiblock agent (Polybatch® SAB-1982VA). The first layer of the control sample comprised about 50.0 wt. % of EMA (Lotryl® 20MA08), about 48.0 wt. % of PP-elastomers (Vistamaxx® 3980FL), and about 2.0 wt. % of slip and antiblock agent (Polybatch® SAB-1982VA).

Figure 10:
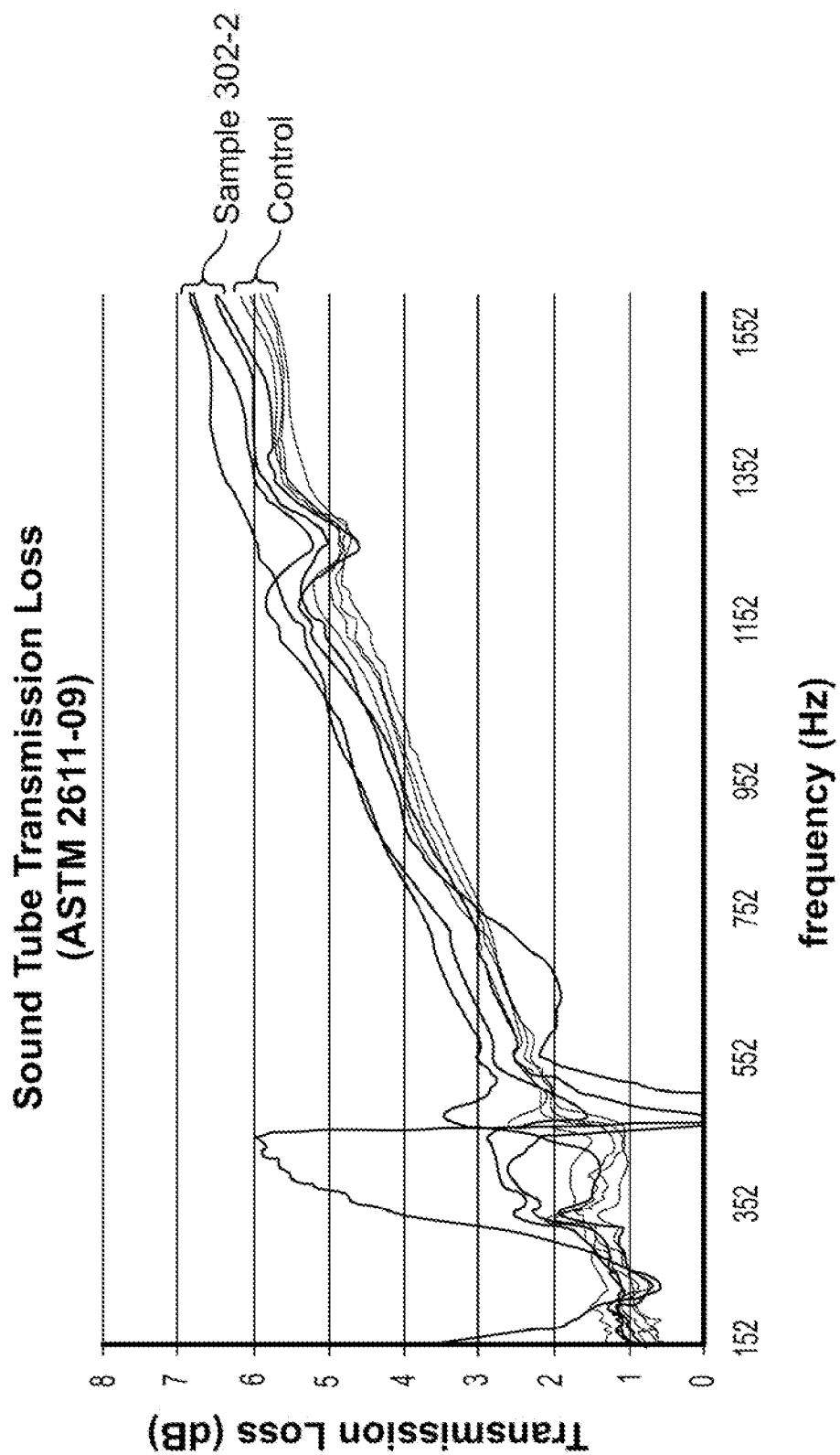
FIG. 10 is a graph showing sound transmission loss data for laminate samples including barium sulfate.
Figure 11:
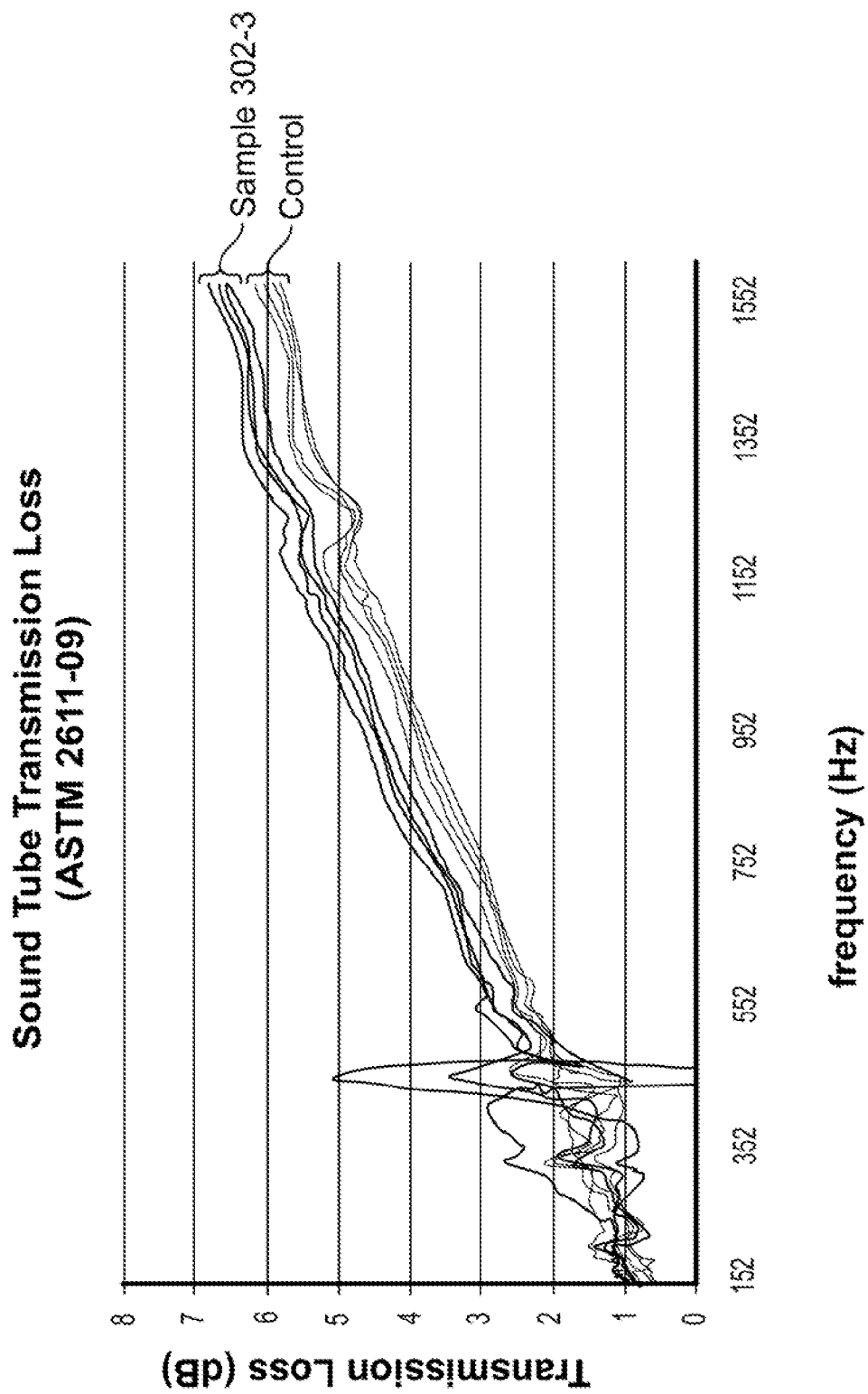
FIG. 11 is graph showing sound transmission loss data for laminate samples including talc.

Multiple samples of Sample 302-2, Sample 303-3, and Control were tested according to ASTM E2611-09. The sound tube transmission loss test data for these samples are plotted and shown in FIGS. 10 and 11. The sound transmission loss expressed in decibel (dB) shows the degree of sound reduced or absorbed by the samples. FIG. 10 shows the sound transmission loss data of Sample 302-2 samples and the control samples. FIG. 11 shows the sound transmission loss data of Sample 302-3 samples and the control samples. As shown in FIGS. 10 and 11, Sample 302-2 including a second layer comprising about 30 wt. % barium sulfate and Sample 302-3 including a second layer comprising about 30 wt. % talc have higher sound transmission loss data than the control samples, which did not include any filler. Thus, a composite film including at least one layer comprising a filler, such as barium sulfate or talc, can provide better sound absorbing properties than those that do not include a filler.

Additional multilayer film samples including an outer foam layer and a gas barrier layer were prepared and tested for their mechanical and sound absorbing properties.

TABLE 4

| | Multilayer Film Samples | | | | | | |
|---|---|---|---|---|---|---|---|
| Sample Code | Skin (Foam) | Inner-2 (Foam) | Inner-1 (Foam) | Tie 1 | Barrier | Tie 2 | Seal |
| X3299-1 (280 μm) | 50% Hybrar ® 7125 + 46% Lotryl ® 20MA08 + 2% Safoam ® FP-20 + 2% Polybatch ® SAB-1982VA | 232 μm 65% Hybrar ® 7125 + 34% EMAC ® 2207 + 1% Safoam ® FP-20 | 65% Hybrar ® 7125 + 34% EMAC ® 2207 + 1% Safoam ® FP-20 | (a*) 80% Lotryl ® 18MA02 + 20% Bynel ® CXA41E710 | (b*) 85% Selar ® PA3426R + 15% Lotader ® 4720 | (a*) same as Tie 1 | 25 μm 50% Lotryl ® 20MA08 + 48% Vistamaxx ® 3980FL + 2% Polybatch ® SAB-1982VA |

TABLE 4-continued

Multilayer Film Samples

| | | | | | | | | |
|---|---|---|---|---|---|---|---|---|
| X3300-1 (288 μm) | 50% Hybrar® 7125 + 46% Lotryl® 20MA08 + 2% Safoam® FPE-20 + 2% Polybatch® SAB-1982VA | 232 μm | 65% Hybrar® 7125 + 34% EMAC® 2207 + 1% Safoam® FPE-20 | 65% Hybrar® 7125 + 34% EMAC® 2207 + 1% Safoam® FPE-20 | (a*) 80% Lotryl® 18MA02 + 20% Bynel® CXA41E710 | (b*) 85% Selar® PA3426R + 15% Lotader® 4720 | (a*) same as Tie 1 | 25 μm 50% Lotryl® 20MA08 + 48% Vistamaxx® 3980FL + 2% Polybatch® SAB-1982VA |
| X3301-1 (294 μm) | 50% Hybrar® 7125 + 46% Lotryl® 20MA08 + 2% Expancel® 950MB80 + 2% Polybatch® SAB-1982VA | 261 μm | 65% Hybrar® 7125 + 34% EMAC® 2207 + 1% Expancel® 950MB80 | 65% Hybrar® 7125 + 34% EMAC® 2207 + 1% Expancel® 950MB80 | (a*) 80% Lotryl® 18MA02 + 20% Bynel® CXA41E710 | (b*) 85% Selar® PA3426R + 15% Lotader® 4720 | (a*) same as Tie 1 | 17 μm 50% Lotryl® 20MA08 + 48% Vistamaxx® 3980FL + 2% Polybatch® SAB-1982VA |
| X3356-1 (249 μm) | 44% Hybrar® 7125 + 52% EMAC® 2207 + 2% Safoam® FP-20 + 2% Polybatch® SAB-1982VA | 209 μm | 65% Hybrar® 7125 + 34% EMAC® 2207 + 1% Safoam® FP-20 | 65% Hybrar® 7125 + 34% EMAC® 2207 + 1% Safoam® FP-20 | (a*) 80% Lotryl® 18MA02 + 20% Bynel® CXA41E710 | (b*) 85% Selar® PA3426R + 15% Lotader® 4720 | (a*) same as Tie 1 | 28 μm 50% Lotryl® 20MA08 + 48% Vistamaxx® 3980FL + 2% Polybatch® SAB-1982VA |
| X3357-2 (175 μm) | 44% Hybrar® 7125 + 50% EMAC® 2207 + 3% Safoam® FP-20 + 3% Polybatch® SAB-1982VA | 144 μm | 65% Hybrar® 7125 + 34% EMAC® 2207 + 1% Safoam® FP-20 | 65% Hybrar® 7125 + 34% EMAC® 2207 + 1% Safoam® FP-20 | (a*) 80% Lotryl® 18MA02 + 20% Bynel® CXA41E710 | (b*) 85% Selar® PA3426R + 15% Lotader® 4720 | (a*) same as Tie 1 | 19 μm 50% Lotryl® 20MA08 + 48% Vistamaxx® 3980FL + 2% Polybatch® SAB-1982VA |
| X3438 (277 μm) | 50% Hybrar® 7125 + 46% Lotryl® 20MA08 + 0.8% Expancel® 920DU40 + 1% Hyrobrite® 550 + 2.2% Polybatch® SAB-1982VA | 245 μm | 64.2% Hybrar® 7125 + 34% EMAC® 2207 + 0.8% Expancel® 920DU40 + 1% Hyrobrite® 550 | 64.2% Hybrar® 7125 + 34% EMAC® 2207 + 0.8% Expancel® 920DU40 + 1% Hyrobrite® 550 | (a*) 80% Lotryl® 18MA02 + 20% Bynel® CXA41E710 | (b*) 85% Selar® PA3426R + 15% Lotader® 4720 | (a*) same as Tie 1 | 20 μm 50% Lotryl® 20MA08 + 48% Vistamaxx® 3980FL + 2% Polybatch® SAB-1982VA |
| X3537 (221 μm) | 51.5% Hybrar® 7125 + 45% Lotryl® 20MA08 + 1% Expancel® 920DU40 + 0.5% Hyrobrite® 550 + 2% Polybatch® SAB-1982VA | 187 μm | 64.5% Hybrar® 7125 + 34% EMAC® 2207 + 1% Expancel® 920DU40 + 0.5% Hyrobrite® 550 | 64.5% Hybrar® 7125 + 34% EMAC® 2207 + 1% Expancel® 920DU40 + 0.5% Hyrobrite® 550 | (a*) 80% Lotryl® 18MA02 + 20% Bynel® CXA41E710 | (b*) 85% Selar® PA3426R + 15% Lotader® 4720 | (a*) same as Tie 1 | 22 μm 98% EMAC® 2207 + 2% Polybatch® SAB-1982VA |
| X3609C (200 μm) | 51.4% Hybrar® 7125 + 44% Lotryl® 20MA08 + 2.6% (EV(920DU)50) + 2% Polybatch® SAB-1982VA | 158 μm | 65% Hybrar® 7125 + 32.4% EMAC® 2207 + 2.6% (EV(920DU)50) | 65% Hybrar® 7125 + 32.4% EMAC® 2207 + 2.6% (EV(920DU)50) | (a*) 80% Lotryl® 18MA02 + 20% Bynel® CXA41E710 | (b*) 85% Selar® PA3426R + 15% Lotader® 4720 | (a*) same as Tie 1 | 30 μm 98% EMAC® 2207 + 2% Polybatch® SAB-1982VA |
| X3610 (204 μm) | 46% Hybrar® 7125 + 39% Lotryl® 20MA08 + 2.6% (EV(920DU)50) + 2.4% Polybatch® SAB-1982VA + 10% Color MB | 167 μm | 65% Hybrar® 7125 + 32.4% EMAC® 2207 + 2.6% (EV(920DU)50) | 65% Hybrar® 7125 + 32.4% EMAC® 2207 + 2.6% (EV(920DU)50) | (a*) 80% Lotryl® 18MA02 + 20% Bynel® CXA41E710 | (b*) 85% Selar® PA3426R + 15% Lotader® 4720 | (a*) same as Tie 1 | 25 μm 98% EMAC® 2207 + 2% Polybatch® SAB-1982VA |

TABLE 4-continued

Multilayer Film Samples

| | | | | | | | |
|---|---|---|---|---|---|---|---|
| X3629 (199 μm) | 46% Vistamaxx® 6102 + 49.4% EMAC® 2207 + 2.6% (EV(920DU)50) + 2% Polybatch® SAB-1982VA | 165 μm 65% Hybrar® 7125 + 32.4% EMAC® 2207 + 2.6% (EV (920DU)50) | 65% Hybrar® 7125 + 32.4% EMAC® 2207 + 2.6% (EV (920DU)50) | (a*) 80% Lotryl® 18MA02 + 20% Bynel® CXA41E710 | (b*) 85% Selar® PA3426R + 15% Lotader® 4720 | (a*) same as Tie 1 | 22 μm 98% EMAC® 2207 + 2% Polybatch® SAB-1982VA |
| X3630 (198 μm) | 57.2% Infuse® D9107.10 + 38.2% Elvax® 450 + 2.6% (EV(920DU)50) + 2% Polybatch® SAB-1982VA | 163 μm 65% Hybrar® 7125 + 32.4% EMAC® 2207 + 2.6% (EV (920DU)50) | 65% Hybrar® 7125 + 32.4% EMAC® 2207 + 2.6% (EV (920DU)50) | (a*) 80% Lotryl® 18MA02 + 20% Bynel® CXA41E710 | (b*) 85% Selar® PA3426R + 15% Lotader® 4720 | (a*) same as Tie 1 | 23 μm 98% EMAC® 2207 + 2% Polybatch® SAB-1982VA |
| X3631 (201 μm) | 51% Vistamaxx® 6102 + 44% Elvax® 450 + 3% (EV(920DU)50) + 2% Polybatch® SAB-1982VA | 170 μm 65% Hybrar® 7125 + 32.4% EMAC® 2207 + 2.6% (EV (920DU)50) | 65% Hybrar® 7125 + 32.4% EMAC® 2207 + 2.6% (EV (920DU)50) | (a*) 80% Lotryl® 18MA02 + 20% Bynel® CXA41E710 | (b*) 85% Selar® PA3426R + 15% Lotader® 4720 | (a*) same as Tie 1 | 19 μm 75% Elvax® 450 + 24% Elvax® 3170A + 1% Polybatch® SAB-1982VA |
| X3632 (200 μm) | 46% Vistamaxx® 6102 + 49% EMAC® 2207 + 3% (EV(920DU)50) + 2% Polybatch® SAB-1982VA | 168 μm 68% Vistamaxx® 6102 + 29% EMAC® 2207 + 3% (EV (920DU)50) | 68% Vistamaxx 6102 + 29% EMAC® 2207 + 3% (EV (920DU)50) | (a*) 80% Lotryl® 18MA02 + 20% Bynel® CXA41E710 | (b*) 85% Selar® PA3426R + 15% Lotader® 4720 | (a*) same as Tie 1 | 20 μm 99% EMAC® 2207 + 1% Polybatch® SAB-1982VA |
| X3633 (201 μm) | 46% Vistamaxx® 6102 + 47% EMAC® 2207 + 5% (EV(920DU)50) + 2% Polybatch® SAB-1982VA | 168 μm 68% Vistamaxx® 6102 + 29% EMAC® 2207 + 3% (EV (920DU)50) | 68% Vistamaxx® 6102 + 29% EMAC® 2207 + 3% (EV (920DU)50) | (a*) 80% Lotryl® 18MA02 + 20% Bynel® CXA41E710 | (b*) 85% Selar® PA3426R + 15% Lotader® 4720 | (a*) same as Tie 1 | 21 μm 99% EMAC® 2207 + 1% Polybatch® SAB-1982VA |
| X3634 (200 μm) | 46% Vistamaxx® 6102 + 47% EMAC® 2207 + 5% (EV(920DU)50) + 2% Polybatch® SAB-1982VA | 168 μm 65% Hybrar® 7125 + 32.4% EMAC® 2207 + 2.6% (EV (920DU)50) | 65% Hybrar® 7125 + 32.4% EMAC® 2207 + 2.6% (EV (920DU)50) | (a*) 80% Lotryl® 18MA02 + 20% Bynel® CXA41E710 | (b*) 85% Selar® PA3426R + 15% Lotader® 4720 | (a*) same as Tie 1 | 19 μm 99% EMAC® 2207 + 1% Polybatch® SAB-1982VA |

| Sample Code | Skin | Inner-2 | Tie 1 | Barrier | Tie 2 | Inner-1 | Seal |
|---|---|---|---|---|---|---|---|
| X3635 (205 μm) | 136 μm 46% Vistamaxx® 6102 + 47% EMAC® 2207 + 5% (EV(920DU)50) + 2% Polybatch® SAB-1982VA | 16 μm 65% Hybrar® 7125 + 32.4% EMAC® 2207 + 2.6% (EV (920DU)50) | (a*) 80% Lotryl® 18MA02 + 20% Bynel® CXA41E710 | (b*) 85% Selar® PA3426R + 15% Lotader® 4720 | (a*) same as Tie 1 | 19 μm 65% Hybrar® 7125 + 32.4% EMAC® 2207 + 2.6% (EV (920DU)50) | 22 μm 99% EMAC® 2207 + 1% Polybatch® SAB-1982VA |

TABLE 4-continued

Multilayer Film Samples

| | | | | | | | |
|---|---|---|---|---|---|---|---|
| X3651 (196 μm) | 134 μm 46% Vistamaxx ® 6102 + 47% EMAC ® 2207 + 5% (EV(920DU)50) + 2% Polybatch ® SAB-1982VA | 15 μm 55% Hybrar ® 7125 + 45% EMAC ® 2207 | (a*) 80% Lotryl ® 18MA02 + 20% Bynel ® CXA41E710 | (b*) 85% Selar ® PA3426R + 15% Lotader ® 4720 | (a*) same as Tie 1 | 18 μm 55% Hybrar ® 7125 + 45% EMAC ® 2207 | 17 μm 99% EMAC ® 2207 + 1% Polybatch ® SAB-1982VA |
| X3652 (210 μm) | 141 μm 46% Vistamaxx ® 6102 + 47% EMAC ® 2207 + 5% (EV(920DU)50) + 2% Polybatch ® SAB-1982VA | 17 μm 55% Hybrar ® 7125 + 45% EMAC ® 2207 | (a*) 80% Lotryl ® 18MA02 + 20% Bynel ® CXA41E710 | (b*) 85% Selar ® PA3426R + 15% Lotader ® 4720 | (a*) same as Tie 1 | 19 μm 55% Hybrar ® 7125 + 45% EMAC ® 2207 | 21 μm 40% Vistamaxx ® 3980FL + 58% Lotryl ® 20MA08 + 2% Polybatch ® SAB-1982VA |
| X3653 (202 μm) | 129 μm 46% Vistamaxx ® 6102 + 49.4% EMAC ® 2207 + 2.6% (EV(920DU)50) + 2% Polybatch ® SAB-1982VA | 16 μm 65% Hybrar ® 7125 + 32.4% EMAC ® 2207 + 2.6% (EV (920DU)50) | (a*) 80% Lotryl ® 18MA02 + 20% Bynel ® CXA41E710 | (b*) 85% Selar ® PA3426R + 15% Lotader ® 4720 | (a*) same as Tie 1 | 19 μm 65% Hybrar ® 7125 + 32.4% EMAC ® 2207 + 2.6% (EV (920DU)50) | 26 μm 40% Vistamaxx ® 3980FL + 58% Lotryl ® 20MA08 + 2% Polybatch ® SAB-1982VA |
| X3654 (144 μm) | 74 μm 46% Vistamaxx ® 6102 + 47% EMAC ® 2207 + 5% (EV(920DU)50) + 2% Polybatch ® SAB-1982VA | 13 μm 55% Hybrar ® 7125 + 45% EMAC ® 2207 | (a*) 80% Lotryl ® 18MA02 + 20% Bynel ® CXA41E710 | (b*) 85% Selar ® PA3426R + 15% Lotader ® 4720 | (a*) same as Tie 1 | 17 μm 55% Hybrar ® 7125 + 45% EMAC ® 2207 | 28 μm 40% Vistamaxx ® 3980FL + 58% Lotryl ® 20MA08 + 2% Polybatch ® SAB-1982VA |
| X3655 (198 μm) | 130 μm 46% Vistamaxx ® 3980FL + 47% Lotryl ® 20MA08 + 5% (EV(920DU)50) + 2% Polybatch ® SAB-1982VA | 14 μm 55% Hybrar ® 7125 + 45% EMAC ® 2207 | (a*) 80% Lotryl ® 18MA02 + 20% Bynel ® CXA41E710 | (b*) 85% Selar ® PA3426R + 15% Lotader ® 4720 | (a*) same as Tie 1 | 17 μm 55% Hybrar ® 7125 + 45% EMAC ® 2207 | 25 μm 40% Vistamaxx ® 3980FL + 58% Lotryl ® 20MA08 + 2% Polybatch ® SAB-1982VA |
| X3656 (153 μm) | 90 μm 46% Vistamaxx ® 3980FL + 47% Lotryl ® 20MA08 + 5% (EV(920DU)50) + 2% Polybatch ® SAB-1982VA | 15 μm 55% Hybrar ® 7125 + 45% EMAC ® 2207 | (a*) 80% Lotryl ® 18MA02 + 20% Bynel ® CXA41E710 | (b*) 85% Selar ® PA3426R + 15% Lotader ® 4720 | (a*) same as Tie 1 | 14 μm 55% Hybrar ® 7125 + 45% EMAC ® 2207 | 22 μm 40% Vistamaxx ® 3980FL + 58% Lotryl ® 20MA08 + 2% Polybatch ® SAB-1982VA |
| X3657 (202 μm) | 130 μm 47% Vistamaxx ® 3980FL + 47% Lotryl ® 20MA08 + 4% Expancel ® 950MB80 + 2% Polybatch ® SAB-1982VA | 15 μm 55% Hybrar 7125 + 45% EMAC2207 | (a*) 80% Lotryl ® 18MA02 + 20% Bynel ® CXA41E710 | (b*) 85% Selar ® PA3426R + 15% Lotader ® 4720 | (a*) same as Tie 1 | 18 μm 55% Hybrar ® 7125 + 45% EMAC ® 2207 | 27 μm 40% Vistamaxx ® 3980FL + 58% Lotryl ® 20MA08 + 2% Polybatch ® SAB-1982VA |

TABLE 4-continued

Multilayer Film Samples

| Sample | | | | | | | |
|---|---|---|---|---|---|---|---|
| X3706 (148 μm) | 88 μm 46% Vistamaxx® 3980FL + 47% Elvaloy® AC1820 + 5% (EV(920DU)50) + 2% Polybatch® SAB-1982VA | 15 μm 65% Hybrar® 7125 + 35% Elvaloy® AC1820 | (a*) 80% Lotryl® 18MA02 + 20% Bynel® CXA41E710 | (b*) 85% Selar® PA3426R + 15% Lotader® 4720 | (a*) same as Tie 1 | 11 μm 65% Hybrar® 7125 + 35% Elvaloy® AC1820 | 19 μm 99% EMAC® 2207 + 1% Polybatch® SAB-1982VA |
| X3707 (158 μm) | 86 μm 46% Vistamaxx® 6202FL + 47% Elvaloy® AC1820 + 5% (EV(920DU)50) + 2% Polybatch® SAB-1982VA | 15 μm 65% Hybrar® 7125 + 35% Elvaloy® AC1820 | (a*) 80% Lotryl® 18MA02 + 20% Bynel® CXA41E710 | (b*) 85% Selar® PA3426R + 15% Lotader® 4720 | (a*) same as Tie 1 | 16 μm 65% Hybrar® 7125 + 35% Elvaloy® AC1820 | 23 μm 99% EMAC® 2207 + 1% Polybatch® SAB-1982VA |
| X3708 (155 μm) | 86 μm 61% Vistamaxx® 6202FL + 32% Elvaloy® AC 1820 + 5% (EV(920DU)50) + 2% Polybatch® SAB-1982VA | 14 μm 65% Hybrar® 7125 + 35% Elvaloy® AC1820 | (a*) 80% Lotryl® 18MA02 + 20% Bynel® CXA41E710 | (b*) 85% Selar® PA3426R + 15% Lotader® 4720 | (a*) same as Tie 1 | 21 μm 65% Hybrar® 7125 + 35% Elvaloy® AC1820 | 30 μm 99% EMAC® 2207 + 1% Polybatch® SAB-1982VA |
| X3709 (157 μm) | 84 μm 61% Vistamaxx® 6202FL + 32% Elvaloy® AC 1820 + 5% (EV(920DU)50) + 2% Polybatch® SAB-1982VA | 18 μm 64% Hybrar® 5127 + 34% Vistamaxx® 6202 + 2% Preadd® AO 181 | (a*) 80% Lotryl® 18MA02 + 20% Bynel® CXA41E710 | (b*) 85% Selar® PA3426R + 15% Lotader® 4720 | (a*) same as Tie 1 | 17 μm 64% Hybrar® 5127 + 34% Vistamaxx® 6202 + 2% Preadd AO 181 | 21 μm 99% EMAC® 2207 + 1% Polybatch® SAB-1982VA |
| X3710 (146 μm) | 88 μm 51% Hybrar® 7125 + 42% Lotryl® 20MA08 + 5% (EV(920DU)50) + 2% Polybatch® SAB-1982VA | 16 μm 64% Hybrar® 5127 + 34% Vistamaxx® 6202 + 2% Preadd® AO 181 | (a*) 80% Lotryl® 18MA02 + 20% Bynel® CXA41E710 | (b*) 85% Selar® PA3426R + 15% Lotader® 4720 | (a*) same as Tie 1 | 16 μm 64% Hybrar® 5127 + 34% Vistamaxx® 6202 + 2% Preadd® AO 181 | 21 μm 99% EMAC® 2207 + 1% Polybatch® SAB-1982VA |
| X3711 (146 μm) | 83 μm 51% Hybrar® 7125 + 42% Lotryl® 20MA08 + 5% (EV(920DU)50) + 2% Polybatch® SAB-1982VA | 17 μm 65% Vistamaxx® 6102 + 35% Lotryl® 20MA08 | (a*) 80% Lotryl® 18MA02 + 20% Bynel® CXA41E710 | (b*) 85% Selar® PA3426R + 15% Lotader® 4720 | (a*) same as Tie 1 | 14 μm 65% Vistamaxx® 6102 + 35% Lotryl® 20MA08 | 22 μm 99% EMAC® 2207 + 1% Polybatch® SAB-1982VA |
| X3712 (150 μm) | 85 μm 51% Hybrar® 7125 + 42% Lotryl® 20MA08 + 5% (EV(920DU)50) + 2% Polybatch® SAB-1982VA | 18 μm 85% Vistamaxx® 3980 + 15% Lotryl® 20MA08 | (a*) 80% Lotryl® 18MA02 + 20% Bynel® CXA41E710 | (b*) 85% Selar® PA3426R + 15% Lotader® 4720 | (a*) same as Tie 1 | 14 μm 85% Vistamaxx® 3980 + 15% Lotryl® 20MA08 | 24 μm 99% EMAC® 2207 + 1% Polybatch® SAB-1982VA |
| X3713 (130 μm) | 81 μm 47% Vistamaxx® 3980 + 46% Lotryl® 20MA08 + 5% (EV(920DU)50) + 2% Polybatch® SAB-1982VA | 18 μm 64% Hybrar® 5127 + 34% Vistamaxx® 6202 + 2% Preadd® AO 181 | (a*) 80% Lotryl® 18MA02 + 20% Bynel® CXA41E710 | (b*) 85% Selar® PA3426R + 15% Lotader® 4720 | (a*) same as Tie 1 | 12 μm 64% Hybrar® 5127 + 34% Vistamaxx® 6202 + 2% Preadd® AO 181 | 19 μm 99% EMAC® 2207 + 1% Polybatch® SAB-1982VA |

TABLE 4-continued

Multilayer Film Samples

| | | | | | | | |
|---|---|---|---|---|---|---|---|
| X3714 (148 μm) | 68 μm 38% Vistamaxx ® 3980 + 57.5% Lotryl ® 20MA08 + 2.5% (EV(920DU)50) + 2% Polybatch ® SAB-1982VA | 17 μm 64% Hybrar ® 5127 + 34% Vistamaxx ® 6202 + 2% Preadd ® AO 181 | (a*) 80% Lotryl ® 18MA02 + 20% Bynel ® CXA41E710 | (b*) 85% Selar ® PA3426R + 15% Lotader ® 4720 | (a*) same as Tie 1 | 21 μm 64% Hybrar ® 5127 + 34% Vistamaxx ® 6202 + 2% Preadd ® AO 181 | 9 μm 99% EMAC ® 2207 + 1% Polybatch ® SAB-1982VA |
| X3715 (160 μm) | 69 μm 38% Vistamaxx ® 3980 + 56.5% Elvaloy ® AC1820 + 2.5% (EV(920DU)50) + 2% Polybatch ® SAB-1982VA + 1% Polyone ® FDM 55802 | 42 μm 65% Hybrar ® 7125 + 35% Elvaloy ® AC1820 | (a*) 80% Lotryl ® 18MA02 + 20% Bynel ® CXA41E710 | (b*) 85% Selar ® PA3426R + 15% Lotader ® 4720 | (a*) same as Tie 1 | 13 μm 65% Hybrar ® 7125 + 35% Elvaloy ® AC1820 | 11 μm 99% EMAC ® 2207 + 1% Polybatch ® SAB-1982VA |
| X3716 (151 μm) | 72 μm 38% Vistamaxx ® 3980 + 57% Elvaloy ® AC1820 + 1.5% (EV(920DU)50) + 2% Polybatch ® SAB-1982VA + 1.5% Polyone ® FDM 55802 | 39 μm 65% Hybrar ® 7125 + 35% Elvaloy ® AC1820 | (a*) 80% Lotryl ® 18MA02 + 20% Bynel ® CXA41E710 | (b*) 85% Selar ® PA3426R + 15% Lotader ® 4720 | (a*) same as Tie 1 | 13 μm 65% Hybrar ® 7125 + 35% Elvaloy ® AC1820 | 14 μm 99% EMAC ® 2207 + 1% Polybatch ® SAB-1982VA |
| X3717 (157 μm) | 69 μm 38% Vistamaxx ® 3980 + 56.5% Elvaloy ® AC1820 + 1.5% (EV(920DU)50) + 2% Polybatch ® SAB-1982VA + 2% Polyone ® FDM 55802 | 43 μm 65% Hybrar ® 7125 + 35% Elvaloy ® AC1820 | (a*) 80% Lotryl ® 18MA02 + 20% Bynel ® CXA41E710 | (b*) 85% Selar ® PA3426R + 15% Lotader ® 4720 | (a*) same as Tie 1 | 10 μm 65% Hybrar ® 7125 + 35% Elvaloy ® AC1820 | 15 μm 99% EMAC ® 2207 + 1% Polybatch ® SAB-1982VA |

(a*), thickness - 3 μm to 5 μm
(b*), thickness - 3 μm to 5 μm

The first 15 samples in Table 4 (X3299-1, X3300-1, X3301-1, X3356-1, X3357-2, X3438, X3537, X3609C, X3610, X3629, X3630, X3631, X3632, X3633, X3634) were seven layer films having a foam/foam/foam/tie/barrier/tie/seal configuration similar to the seven-layer film 140 of FIG. 4. Each of the foam layers included a foaming agent, such as, Safoam® FP-20, Expancel® 950MB80, Expancel®920DU40 from Akzo, or EV(920DU)50 from Polychem Dispersion.

Samples X3299-1, X3300-1, and X3301-1 were made using the same materials as samples X3299, X3300, X3301, respectively, but were configured to have a different thickness. X3299-1 had a total thickness of about 280 μm±10%, in which the three foam layers together had a thickness of about 232 μm±10%, each of the barrier and tie layers had a thickness of about 3-5 μm±10%, and the seal layer had a thickness of about 25 μm±10%. All thicknesses provided in Table 4 had a tolerance of ±10%, thus, the tolerance will not be repeated hereinbelow. X3300-1 had a total thickness of about 288 μm, in which the three foam layers together had a thickness of about 232 μm, each of the barrier and tie layers had a thickness of about 3-5 μm, and the seal layer had a thickness of about 25 μm. X3301-1 had a total thickness of about 294 μm, in which the three foam layers together had a thickness of about 261 μm, each of the barrier and tie layers had a thickness of about 3-5 μm, and the seal layer had a thickness of about 17 μm.

Sample X3356-1 had a total thickness of about 249 μm, in which the three foam layers together had a thickness of about 209 μm, each of the barrier and tie layers had a thickness of about 3-5 μm, and the seal layer had a thickness of about 28 μm. The outer foam layer was formed from a blend comprising about 44 wt. % of vinyl-bond rich SEPS block copolymer (Hybrar® 7125), about 52 wt. % of EMA (EMAC® 2207), about 2 wt. % of blowing agent (Safoam® FP-20), and about 2 wt. % of slip and antiblock agent (Polybatch® SAB-1982VA). Each of the two inner foam layers was formed from a blend comprising about 65 wt. % of vinyl-bond rich SEPS block copolymer (Hybrar® 7125), about 34 wt. % of EMA (EMAC® 2207), and about 1 wt. % of blowing agent (Safoam® FP-20). Each of the tie layers was formed from a blend comprising about 80 wt. % EMA (Lotryl® 18MA02) and about 20 wt. % MAH grafted LLDPE (Bynel® CXA41E710). The barrier layer was formed from a blend comprising about 85 wt. % amorphous polyamide (Selar® PA3426R) and about 15 wt. % functionalized rubber blend (Lotader® 4720). The seal layer was formed from a blend comprising about 50 wt. % of EMA (Lotryl® 20MA08), about 48 wt. % of PP-elastomers (Vistamaxx® 3980FL), and about 2 wt. % of a slip and antiblock agent (Polybatch® SAB-1982VA).

Sample X3357-2 had a total thickness of about 175 µm, in which the three foam layers together had a thickness of about 144 µm, each of the barrier and tie layers had a thickness of about 3-5 µm, and the seal layer had a thickness of about 19 µm. The outer foam layer was formed from a blend comprising about 44 wt. % of vinyl-bond rich SEPS block copolymer (Hybrar® 7125), about 50 wt. % of EMA (EMAC® 2207), about 3 wt. % of blowing agent (Safoam® FP-20), and about 3 wt. % of slip and antiblock agent (Polybatch® SAB-1982VA). The two inner foam layers, two tie layers, barrier layer, and seal layer were formed from the same polymer blends used to make the respective layers of X3356-1.

Sample X3438 had a total thickness of about 277 µm, in which the three foam layers together had a thickness of about 245 µm, each of the barrier and tie layers had a thickness of about 3-5 µm, and the seal layer had a thickness of about 20 µm. The outer foam layer was formed from a blend comprising about 50 wt. % of vinyl-bond rich SEPS block copolymer (Hybrar® 7125), about 46 wt. % of EMA (Lotryl® 20MA08), about 0.8 wt. % of foam microspheres (Expancel® 920DU40), 1% white mineral oil (Hybrobrite®550 from Sonneborn), and about 2.2 wt. % of slip and antiblock agent (Polybatch® SAB-1982VA). Each of the two inner foam layers was formed from a blend comprising about 64.2 wt. % of vinyl-bond rich SEPS block copolymer (Hybrar® 7125), about 34 wt. % of EMA (EMAC® 2207), and about 0.8 wt. % of foam microspheres (Expancel® 920DU40), 1% white mineral oil (Hybrobrite® 550). The two tie layers, barrier layer, and seal layer were formed from the same polymer blends used to make the respective layers of X3356-1.

Sample X3438 had a total thickness of about 277 µm, in which the three foam layers together had a thickness of about 245 µm, each of the barrier and tie layers had a thickness of about 3-5 µm, and the seal layer had a thickness of about 20 µm. The outer foam layer was formed from a blend comprising about 50 wt. % of vinyl-bond rich SEPS block copolymer (Hybrar® 7125), about 46 wt. % of EMA (Lotryl® 20MA08), about 0.8 wt. % of foam microspheres (Expancel® 920DU40), 1% white mineral oil (Hybrobrite® 550 from Sonneborn), and about 2.2 wt. % of slip and antiblock agent (Polybatch® SAB-1982VA). Each of the two inner foam layers was formed from a blend comprising about 64.2 wt. % of vinyl-bond rich SEPS block copolymer (Hybrar® 7125), about 34 wt. % of EMA (EMAC® 2207), and about 0.8 wt. % of foam microspheres (Expancel® 920DU40), 1% white mineral oil (Hybrobrite®550). The two tie layers, barrier layer, and seal layer were formed from the same polymer blends used to make the respective layers of X3356-1.

Similarly, samples X3537, X3609C, X3610, X3629, X3630, X3631, X3632, X3633, and X3634 were formed using polymer blends. The film constructions of these samples are summarized in Table 4 above. As shown, at least one foam layer of the film samples disclosed in Table 4 included vinyl-bond rich SEPS block copolymer (Hybrar® 7125), except samples X3632 and X3633, which did not include a vinyl-bond rich triblock copolymer in any of the layers.

Sample X3632 had a total thickness of about 200 µm, in which the three foam layers together had a thickness of about 168 µm, each of the barrier and tie layers had a thickness of about 3-5 µm, and the seal layer had a thickness of about 20 µm. The outer foam layer was formed from a blend comprising about 46 wt. % of ethylene-propylene copolymer (Vistamaxx® 6102), about 49 wt. % of EMA (EMAC® 2207), about 3 wt. % of masterbatch containing 50% Expancel® 920DU40 microspheres (EV(920DU)50), and about 2 wt. % of slip and antiblock agent (Polybatch® SAB-1982VA). Each of the two inner foam layers was formed from a blend comprising about 68 wt. % of ethylene-propylene copolymer (Vistamaxx® 6102), about 29 wt. % of EMA (EMAC® 2207), and about 3 wt. % of masterbatch containing 50% Expancel® 920DU40 microspheres (EV(920DU)50). The two tie layers and barrier layer were formed from the same polymer blends used to make the respective layers of X3356-1. The seal layer was formed of a blend comprising about 99 wt. % of EMA (EMAC® 2207) and about 1 wt. % of a slip and antiblock agent (Polybatch® SAB-1982VA).

Sample X3633 had a total thickness of about 201 µm, in which the three foam layers together had a thickness of about 168 µm, each of the barrier and tie layers had a thickness of about 3-5 µm, and the seal layer had a thickness of about 21 µm. The outer foam layer was formed from a blend comprising about 46 wt. % of ethylene-propylene copolymer (Vistamaxx® 6102), about 47 wt. % of EMA (EMAC® 2207), about 5 wt. % of masterbatch containing 50% Expancel® 920DU40 microspheres (EV(920DU)50), and about 2 wt. % of slip and antiblock agent (Polybatch® SAB-1982VA). The two inner foam layers, two tie layers, barrier layer, and seal layer were formed from the same polymer blends used to make the respective layers of X3632.

Figure 12:
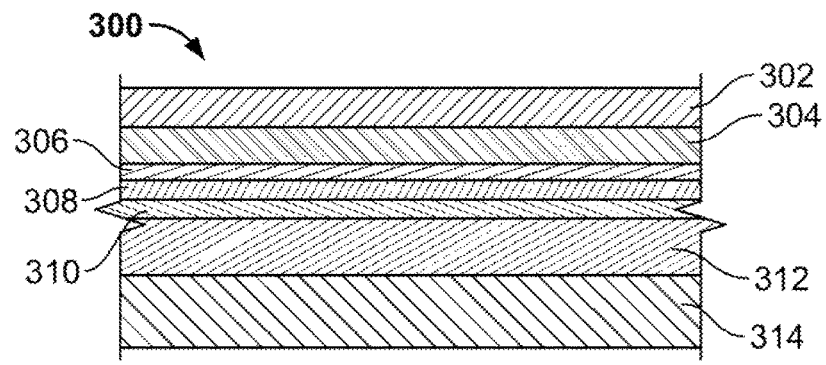
FIG. 12 is a cross-sectional illustration of a seven-layer film according to an embodiment.

Samples X3635, X3651, X3652, X3653, X3654, X3655, X3656, X3657, X3706, X3707, X3708, X3709, X3710, X3711, X3712, X3713, X3714, X3715, X3716, and X3717 were also seven-layer films, but these film samples had a different film construction than the foregoing film samples. These film samples had a seal (302)/inner-1 (304)/tie (306)/barrier (308)/tie (310)/inner-2 (312)/outer foam (314) construction similar to a multilayer film 300 shown in FIG. 12. In these samples, the two inner layers may or may not be foam layers. For example, the inner layers of sample X3635 and X3653 were foam layers comprising a foaming agent, while the inner layers of the other samples were not foam layers.

Further, at least one of the outer foam layer and inner layers of these film samples included a vinyl-bond rich triblock copolymer for sound absorbing properties. The film constructions of these samples are summarized in Table 4 above.

Figure 13:
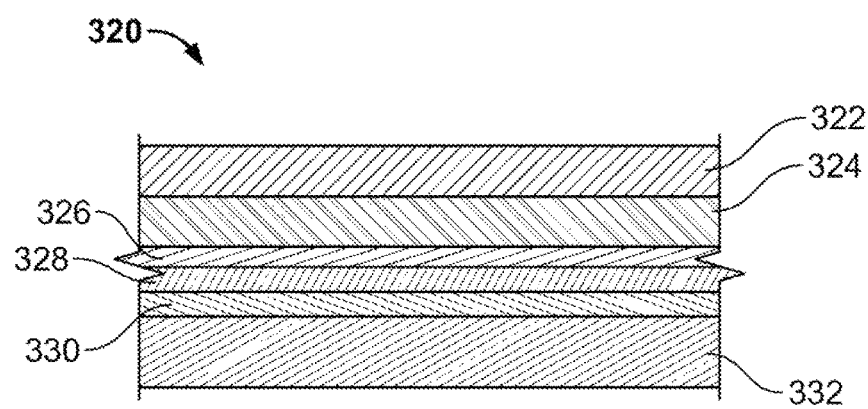
FIG. 13 is a cross-sectional illustration of a six-layer film according to an embodiment.
Figure 14:
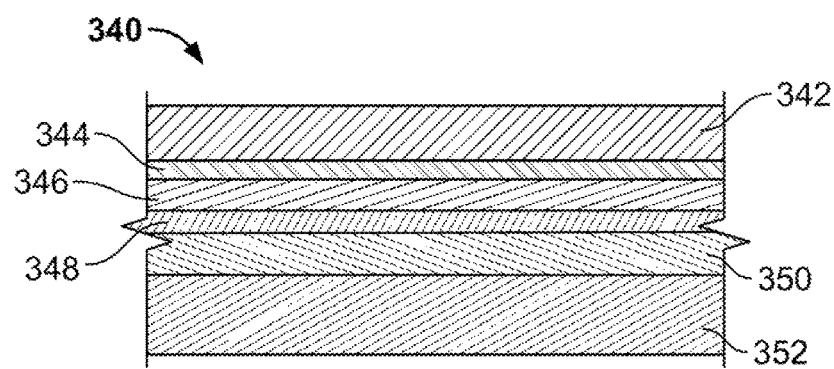
FIG. 14 is a cross-sectional illustration of a six-layer film according to another embodiment.

Other multilayer film embodiments may include a vinyl-bond rich triblock copolymer in a tie, barrier, or seal layer. The multilayer films may also be configured to have different layer constructions. For examples, a multilayer film may be configured similar to a six-layer film 320 shown in FIG. 13, which has a seal (322)/inner (324)/tie (326)/barrier (328)/tie (330)/foam (332) construction. In another example, a multilayer foam film may have a seal (342)/tie (344)/barrier (346)/tie (348)/inner (350)/foam (352) construction similar to a six-layer film 340 of FIG. 14. The inner layers of these multilayer films may or may not be a foam layer.

Film properties of the multilayer film samples were evaluated and summarized in Table 5.

TABLE 5

Film Properties of Multilayer Foam Film Samples

| Film Codes | Thickness, um | Elmendorf Tear, gf/mil | | Tensile Strength (psi) | | Elongation at Break (%) | | Modulus (1000 psi) | | Film Noise SPL(A) dB |
|---|---|---|---|---|---|---|---|---|---|---|
| | | MD | CD | MD | CD | MD | CD | MD | CD | |
| X3299-1 | 280 | 209 | 120 | 1000 | 965 | 628 | 746 | 6.8 | 5.5 | 34.8 |
| X3300-1 | 288 | 217 | 143 | 951 | 937 | 746 | 745 | 5.0 | 4.8 | 32.2 |
| X3301-1 | 294 | 127 | 89 | 626 | 586 | 532 | 679 | 5.3 | 3.8 | 29.8 |
| X3356-1 | 249 | 212 | 112 | 1106 | 1035 | 657 | 745 | 7.2 | 6.0 | 31.9 |
| X3357-2 | 175 | 73 | 45 | 667 | 464 | 264 | 506 | 8.8 | 7.4 | 49.9 |
| X3438 | 277 | 211 | 140 | 740 | 776 | 544 | 745 | 5.1 | 3.6 | 32.4 |
| X3537 | 221 | 138 | 59 | 624 | 769 | 362 | 745 | 5.2 | 3.9 | 32.2 |
| X3609C | 200 | 199 | 70 | 667 | 841 | 315 | 745 | 5.8 | 4.7 | 37.8 |
| X3610 | 204 | 192 | 87 | 653 | 841 | 315 | 745 | 6.1 | 5.0 | 40.5 |
| X3629 | 199 | 88 | 48 | 769 | 870 | 405 | 745 | 7.7 | 7.0 | 36.6 |
| X3630 | 198 | 94 | 58 | 769 | 812 | 251 | 745 | 9.1 | 6.9 | 38.8 |
| X3631 | 201 | 141 | 25 | 740 | 1059 | 291 | 745 | 7.9 | 6.4 | 41.8 |
| X3632 | 200 | 99 | 21 | 957 | 972 | 669 | 741 | 5.0 | 4.9 | 37.3 |
| X3633 | 201 | 85 | 20 | 754 | 812 | 470 | 703 | 5.6 | 4.5 | 35.8 |
| X3634 | 200 | 107 | 20 | 653 | 827 | 289 | 727 | 6.0 | 5.5 | 37.9 |
| X3635 | 205 | 164 | 29 | 769 | 914 | 448 | 734 | 5.4 | 4.2 | 38.0 |
| X3651 | 196 | 151 | 28 | 812 | 899 | 554 | 717 | 5.0 | 4.2 | 37.0 |
| X3652 | 210 | 180 | 40 | 986 | 957 | 641 | 738 | 5.6 | 4.4 | 40.3 |
| X3653 | 202 | 189 | 31 | 1015 | 1059 | 597 | 737 | 6.3 | 5.6 | 41.7 |
| X3654 | 144 | 151 | 35 | 943 | 1030 | 489 | 732 | 5.7 | 4.9 | 44.2 |
| X3655 | 198 | 179 | 50 | 827 | 769 | 537 | 619 | 7.8 | 6.5 | 36.3 |
| X3656 | 153 | 153 | 43 | 972 | 841 | 524 | 607 | 8.1 | 6.5 | 38.8 |
| X3657 | 202 | 87 | 44 | 667 | 479 | 452 | 475 | 6.7 | 5.1 | 32.1 |
| X3706 | 148 | 139 | 37 | 1218 | 1247 | 588 | 708 | 8.3 | 7.4 | 43.7 |
| X3707 | 158 | 156 | 77 | 783 | 885 | 340 | 743 | 5.7 | 4.7 | 46.5 |
| X3708 | 155 | 55 | 62 | 783 | 885 | 370 | 744 | 5.5 | 4.8 | 44.3 |
| X3709 | 157 | 22 | 21 | 682 | 827 | 331 | 654 | 5.5 | 4.6 | 48.8 |
| X3710 | 146 | 73 | 58 | 624 | 682 | 306 | 641 | 4.1 | 3.3 | 46.6 |
| X3711 | 146 | 75 | 42 | 1088 | 899 | 698 | 742 | 4.5 | 3.5 | 48.3 |
| X3712 | 150 | 171 | 79 | 1131 | 1044 | 602 | 718 | 6.4 | 5.4 | 45.1 |
| X3713 | 130 | 78 | 34 | 841 | 885 | 381 | 603 | 7.2 | 5.9 | 40.6 |
| X3714 | 148 | 32 | 30 | 783 | 943 | 363 | 649 | 6.7 | 5.5 | 40.5 |
| X3715 | 160 | 87 | 30 | 754 | 783 | 637 | 435 | 4.7 | 5.5 | 41.1 |
| X3716 | 151 | 96 | 35 | 899 | 986 | 466 | 683 | 5.6 | 5.1 | 41.4 |
| X3717 | 157 | 108 | 26 | 841 | 1044 | 318 | 709 | 6.8 | 5.9 | 43.6 |

As summarized in Table 4 and Table 5, the multilayer film samples were relatively thin films having a total thickness of about 130 μm (5.1 mil) to about 300 μm (11.8 mil), and included at least an outer foam layer and a gas barrier layer. In other embodiments, the multilayer film may be configured to have a total thickness of about 50 μm (2.0 mil) to about 800 μm (31.5 mil), preferably about 100 μm (3.9 mil) to about 500 μm (19.7 mil), and more preferably about 120 μm (4.7 mil) to about 350 μm (13.8 mil). The multilayer film samples had good mechanical properties as exhibited by Elmendorf tear, tensile strength, and elongation at break test result. Further, the multilayer film samples had softness suitable for ostomy, packaging and many other similar applications. The multilayer film samples were tested according to ASTM D882. As summarized in Table 5, the multilayer film samples had a modulus of about 3 ksi to about 8 ksi. In other embodiments, the multilayer film may have a modulus of about 2 ksi to about 40 ksi. Further, the multilayer film samples had relatively low film noise levels of about 30 dB to about 50 dB.

In the present disclosure, the words "a" or "an" are to be taken to include both the singular and the plural. Conversely, any reference to plural items shall, where appropriate, include the singular. All of the concentrations noted herein as percentage are percent by weight unless otherwise noted.

From the foregoing it will be observed that numerous modifications and variations can be effectuated without departing from the true spirit and scope of the novel concepts of the present invention. It is to be understood that no limitation with respect to the specific embodiments illustrated is intended or should be inferred. The disclosure is intended to cover by the appended claims all such modifications as fall within the scope of the claims.

What is claimed is:

1. A multilayer film including two outer layers and a gas barrier layer, wherein the gas barrier layer is arranged between the outer layers, and at least one of the outer layers is a foam layer, and wherein the multilayer film has an elastic modulus of about 2 ksi to about 9.1 ksi when measured according to ASTM D882 and a thickness of about 120 μm to about 350 μm.

2. The multilayer film of claim 1, further including at least one tie layer and at least one inner layer.

3. The multilayer film of claim 2, wherein the multilayer film is a six-layer film having a seal layer/tie layer/barrier layer/tie layer/inner layer/outer foam layer construction.

4. The multilayer film of claim 3, wherein the inner layer is a foam layer.

5. The multilayer film of claim 2, wherein the multilayer film is a seven-layer film having a seal layer/tie layer/barrier layer/tie layer/inner layer/inner layer/outer foam layer construction.

6. The multilayer film of claim 5, wherein at least one of the inner layers is a foam layer.

7. The multilayer film of claim 2, wherein the multilayer film is a seven-layer film having a seal layer/inner layer/tie layer/barrier layer/tie layer/inner layer/outer foam layer construction.

8. The multilayer film of claim 7, wherein at least one of the inner layers is a foam layer.

9. The multilayer film of claim 2, wherein the multilayer film is a six-layer film having a seal layer/inner layer/tie layer/barrier layer/tie layer/outer foam layer construction.

10. The multilayer film of claim 9, wherein the inner layer is a foam layer.

11. The multilayer film of claim 2, wherein the multilayer film is a five-layer film having a seal layer/tie layer/barrier layer/tie layer/outer foam layer construction.

12. The multilayer film of claim 1, wherein the outer foam layer is formed from a polymer selected from ethylene vinyl acetate (EVA), ethylene methyl acrylate (EMA), ethylene alpha olefin copolymers, ethylene based elastomers, ethylene-propylene (EP) copolymers, and blends thereof, and a foaming agent.

13. The multilayer film of claim 1, wherein the gas barrier layer comprises a polymer selected from polyvinylidene chloride, vinylidene copolymer, polyamide, and ethylene-vinyl alcohol copolymer.

14. The multilayer film of claim 13, wherein the gas barrier layer is formed from a polymer blend comprising an amorphous polyamide and a functionalized rubber blend or compound.

15. The multilayer film of claim 2, wherein at least one of the outer foam layer, inner layers, tie layers, and barrier layer comprises a vinyl-bond rich triblock copolymer.

16. An ostomy pouch comprising an outer wall and a bodyside wall, wherein at least one of the outer wall and the bodyside wall is formed from the multilayer film of claim 1.

* * * * *